(12) United States Patent
Ausen et al.

(10) Patent No.: US 7,001,475 B2
(45) Date of Patent: Feb. 21, 2006

(54) FILM STRUCTURES AND METHODS OF MAKING FILM STRUCTURES

(75) Inventors: Ronald Wayne Ausen, St. Paul, MN (US); Sundaravel Damodaran, Maplewood, MN (US); Hak-Rhim Han, Newport, MN (US); David Wayne Hegdahl, White Bear Lake, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 395 days.

(21) Appl. No.: 10/016,544

(22) Filed: Dec. 11, 2001

(65) Prior Publication Data

US 2003/0124291 A1   Jul. 3, 2003

(51) Int. Cl.
 B32B 31/00 (2006.01)
 B32B 31/14 (2006.01)
 B32B 31/30 (2006.01)

(52) U.S. Cl. ............... 156/229; 156/250; 156/252; 156/253; 156/256; 156/257; 156/295

(58) Field of Classification Search ........... 156/229, 156/250–253, 256–259, 268, 295, 494, 510, 156/515; 264/DIG. 47
See application file for complete search history.

(56) References Cited

U.S. PATENT DOCUMENTS

| | | |
|---|---|---|
| 2,714,562 A | 8/1955 | Hechtman |
| 3,301,741 A | 1/1967 | Henrickson et al. |
| 3,314,838 A | 4/1967 | Erwin |
| 3,331,729 A | 7/1967 | Danielson et al. |
| 3,379,562 A | 4/1968 | Freeman |
| 3,554,835 A | 1/1971 | Morgan |
| 3,857,731 A | 12/1974 | Merrill, Jr. et al. |
| 4,414,970 A * | 11/1983 | Berry .................... 602/75 |
| 4,537,809 A * | 8/1985 | Ang et al. ............. 428/42.2 |
| 4,556,595 A | 12/1985 | Ochi |
| 4,567,011 A * | 1/1986 | Nalle, Jr. .............. 264/504 |
| 4,626,460 A * | 12/1986 | Duncan ................ 428/41.4 |
| 4,736,843 A | 4/1988 | Leonard |
| 4,894,060 A | 1/1990 | Nestegard |
| 4,959,264 A | 9/1990 | Dunk et al. |
| 5,238,736 A | 8/1993 | Tseng et al. |
| 5,240,761 A | 8/1993 | Calhoun et al. |
| 5,344,693 A | 9/1994 | Sanders |
| 5,529,829 A * | 6/1996 | Koskenmaki et al. ....... 428/167 |
| 5,537,723 A | 7/1996 | Yoshida et al. |
| 5,650,215 A | 7/1997 | Mazurek et al. |
| 5,839,634 A | 11/1998 | Pollard et al. |
| 5,866,220 A | 2/1999 | Rusincovitch et al. |
| 5,871,607 A | 2/1999 | Hamilton et al. |
| 5,948,493 A | 9/1999 | Groeger |
| 5,965,235 A | 10/1999 | McGuire et al. |

(Continued)

FOREIGN PATENT DOCUMENTS

GB    975783    11/1964

(Continued)

*Primary Examiner*—Jeff H. Aftergut
*Assistant Examiner*—Justin Fischer
(74) *Attorney, Agent, or Firm*—William J. Bond

(57) ABSTRACT

A method of making a three-dimensional film structure having controllable contact properties comprises making separable surface elements on a top portion of a film structure and stretching the film structure to separate the separable surface elements, thereby obtaining a desired surface structure which delivers a certain contact property such as a pressure sensitive adhesive property. The separable surface elements are provided using a cut film surface, a stemmed film, or a layer of particles.

21 Claims, 7 Drawing Sheets

U.S. PATENT DOCUMENTS

| | | |
|---|---|---|
| 6,020,062 A | 2/2000 | Questel et al. |
| 6,022,612 A | 2/2000 | Wilkie |
| 6,063,482 A | 5/2000 | Peiffer et al. |
| 6,099,940 A | 8/2000 | Hamilton et al. |
| 6,256,788 B1 | 7/2001 | Loewer et al. |
| 6,514,597 B1 | 2/2003 | Strobel et al. |
| 2003/0121586 A1 | 7/2003 | Mitra et al. |

FOREIGN PATENT DOCUMENTS

| | | | |
|---|---|---|---|
| GB | 2205526 | * | 12/1988 |
| GB | 2 285 570 A | | 7/1995 |
| JP | 63106702 | * | 5/1988 |
| WO | WO 97/25256 | | 7/1997 |
| WO | WO 97/25268 | | 7/1997 |
| WO | WO 98/20858 | | 5/1998 |
| WO | WO 98/21410 | | 5/1998 |
| WO | WO 98/50279 | | 11/1998 |
| WO | WO 98/50280 | | 11/1998 |
| WO | WO 98/55109 | | 12/1998 |
| WO | WO 99/17631 | | 4/1999 |

* cited by examiner

FILM STRUCTURES AND METHODS OF MAKING FILM STRUCTURES

CROSS-REFERENCE TO RELATED APPLICATION

This invention is related to a U.S. patent application entitled "Tack-on Pressure Films for Temporary Surface Protection and Surface Modification" (Ser. No. 10/016,541; co-assigned to 3M Innovative Properties Company and concurrently filed with the present application.

TECHNICAL FIELD

This invention relates to single or multilayer film structures used for wrapping, binding, fastening, sealing, labeling or dispensing substances, such as chemicals or drugs. More particularly, this invention relates to film structures having a surface with multiplicity of features including various surface contact properties such as adhesion, controllable by exerting pressure on the film structure.

BACKGROUND OF THE INVENTION

Film structures are widely used for various purposes through surface contact with other objects. Such purposes include wrapping, binding, fastening, sealing and dispensing chemical agents. An operating surface of a film structure may carry an operating agent having a certain operating effect on a target object when the operating agent and the surface of the target object contact each other. One of the most common examples of such film structures is a sheet material having an adhesive operating agent. When the adhesive side is applied on a surface of another object, the sheet material sticks to the contacting surface of the object, forming a bond. Another example is a sheet material having a carrier side containing a chemical or a drug. When the carrier side contacts a surface of an object, the agent (a chemical or a drug) is dispensed to the target surface to take effect on the surface.

In the above described applications, often a user wishes to have control over when, where, how, which part of the film and to what degree the intended operating effect is applied. Traditional film structures do not offer such convenient features. For example, in the art of tapes, labels, and other articles using pressure-sensitive adhesive (PSA) to adhere an adhesive coated surface to a target surface, premature adhesion sometimes is a problem. That is, before the adhesive coated surface can be properly positioned over the target surface, inadvertent contact of the adhesive with the target surface causes premature adhesion at one or more locations, thereby inhibiting proper positioning. Additionally, inadvertent contact between different parts of the same adhesive coated surface can also create problems and waste. Pressure-sensitive adhesive sheet structures (composed of a substrate such as a film or sheet and a pressure sensitive adhesive layer formed on its surface) for example, are employed in a wide range of applications such as signboards, decorative and display applications in automobiles, buildings and containers. Such pressure-sensitive adhesive layers have very high initial adhesion strength, making the adhesion highly uncontrollable. Where the precise positioning of the film structure is required, even skilled workmen experience difficulty in accurately bonding such a pressure sensitive adhesive layer to the desired site in one operation, and removal from the desired site is often necessary. But with a traditional pressure-sensitive adhesive, once the initial contact is made, it is difficult to adjust the position of the film structure.

Another example where more user control is desired is found in thin films commonly used to wrap food. Most commercial food wraps undesirably "cling" to themselves when they are dispensed. Such undesirable properties make the application of the film difficult to control.

Others have attempted to overcome the above described problem of lacking user control. U.S. Pat. No. 5,965,235 to McGuire et al., for example, discloses a three-dimensional sheet material having an application side from which a plurality of spaced three-dimensional protrusions extend outwardly. The protrusions are separated by an interconnected network of three-dimensional spaces between adjacent protrusions. The sheet structure disclosed in McGuire et al. is designed to resist nesting of superimposed layers into one another. The three-dimensional, nesting-resistant sheet materials are manufactured utilizing a three-dimensional forming structure comprising an amorphous pattern of spaced three-dimensional recesses separated by interconnected lands. To manufacture the three-dimensional, nest-resistant sheet materials, a sheet of the formable material is introduced onto the forming structure and permanently deformed into compliance with the forming structure.

PCT Patent WO 97/25268 discloses a substance (such as a drug) delivery system having a three-dimensional structure with outer-most surface features and spaces for containing a substance. The substance has a level below the outermost surface features such that the substance is protected from inadvertent contact with the external surface. The substance remains protected until the three-dimensional structure is sufficiently deformed into the substantially two-dimensional structure and the substances thereby exposed to contact an external surface without compliance of the external surface being necessary. The manufacture of the three-dimensional material includes the steps of coating a substance onto a forming surface, transferring the coating of substance from the forming surface to a piece of material, and forming the piece of material into a three-dimensional structure on the forming surface while the substance is in contact with the forming surface.

A three-dimensional sheet structure similar to that of PCT Patent WO 97/25268 is disclosed in PCT Patent WO 98/55109, in which the sheet structure further provides a selectively-activatible sheet material for dispensing and dispersing a substance (i.e., a drug) onto the target surface. The application side of the sheet material has a plurality of hollow protrusions extending outwardly and separate from one another by valleys, while the opposite side has a plurality of depressions corresponding with the hollow provisions. A substance adheres to and partially fills a location protected from external contact comprising the valleys and/or the depressions. The sheet material may be selectively activated by deforming the hollow progressions to deliver the substance to the target surface.

U.S. Pat. No. 5,240,761 to Calhoun et al. discloses a method of separating a dense monolayer of electrically conductive particles covering an adhesive layer by stretching the adhesive layer. The resultant film has a removable backing layer, and with the backing layer removed, can be used to electrically connect two substrates having electrically conductive elements.

Due to the importance of three-dimensional film structures having controllable contact properties, it is desirable to develop less expensive and more efficient methods of making such film structures, and to provide alternative film structures suitable for a variety of applications.

SUMMARY OF THE INVENTION

One aspect of the present invention provides a method of forming and applying a film structure having controllable surface contact properties. This method comprises: providing a multilayer film structure which has first and second major surfaces and which includes an operating agent therein, the operating agent being spaced from the first major surface of the film structure by a top portion of the film structure, the top portion being defined by predetermined separable surface elements, and the first major surface of the film structure being defined by a plane across separable surface elements; inelastically stretching the multilayer film structure to separate the separable surface elements across the first major surface of the film structure and to increase the exposure of the operating agent through spacings between adjacent separated separable surface elements; applying the first major surface of the film structure to a surface of a substrate; and applying pressure to the second major surface of the film such that the operating agent contacts the structure surface of the substrate.

In one embodiment of the above method, the top portion of the multilayer film structure comprises a layer of particles, each particle defining one of the separable surface elements. In another embodiment of the above method, the film structure includes a top film layer, wherein the top film layer includes the separable surface elements formed by at least partially cutting the top film layer. In yet another embodiment of the above method, the film assembly includes a plurality of stems extending from a continuous portion of the film structure, each stem comprising one of the separable surface elements. Another embodiment of the present invention provides a film structure formed by the above method.

Another aspect of the present invention provides an alternative method of forming and applying a film structure having controllable surface contact properties. This method comprises: providing a film structure which has a first major surface, a second major surface, and a top portion under the first major surface, wherein the top portion includes a plurality of particles; stretching the film structure to separate the particles across the first major surface of the film structure and to increase the exposure of an intermediate surface of the film structure through spacings between adjacent particles; applying the first major surface of the stretched film structure to a surface of a substrate; and applying pressure to the second major surface of the film such that the intermediate surface contacts the surface of the substrate.

In one embodiment of the above method, the film structure further includes an operating agent, which at least partially defines the intermediate surface of the film structure. In one aspect of this embodiment, the operating agent comprises an adhesive. In another aspect of this embodiment, after stretching, each portion of the exposed operating agent is in a layer form having an average thickness, and is spaced from the first surface of the film structure by the particles by an average spacing which is equal to or greater than the average thickness of the corresponding portion of the exposed operating agent.

In another embodiment of the above method, the stretching is inelastic stretching. In another embodiment of the above method, the plurality of particles are electrically non-conductive. In another embodiment of the above method, the film structure is multilayered. In one aspect of this embodiment, the multilayer film structure is formed by coextrusion. In another embodiment of the above method, prior to the stretching step, the plurality of particles defining the top layer of the film structure are arranged in a tightly packed monolayer. In yet another embodiment of the above method, the stretching step includes biaxially stretching the film structure. In one aspect of this embodiment, the stretching step includes simultaneously biaxially stretching the film structure. Another embodiment of the present invention provides a film structure formed by the above method.

Another aspect of the present invention provides a method of forming a film structure. This method comprises: providing a film structure which has a first major surface, a second major surface, and a top portion under the first major surface; cutting the top portion of the film structure such that the top portion defines a plurality of separable surface elements; and stretching the film structure to separate the separable surface elements across the first major surface of the film structure and to increase the exposure of an intermediate surface of the film structure through spacings between adjacent separated separable surface elements.

In one embodiment of the above method, the exposed portions of the intermediate surface form a plurality of recesses, each recess having a recess face spaced from the first major surface and exposed through one of the spacings between adjacent and separated surface elements. In another embodiment of the above method, the film structure further includes an operating agent which at least partially defines the intermediate surface of the film structure. In one aspect of this embodiment, the operating agent is in a layer form adjacent to and beneath the top layer and wherein when the first major surface of the stretched film structure is applied to a surface of a substrate, the operating agent exhibits noticeably greater contact with the surface of the substrate when pressure is applied on the second major surface of the stretched film structure toward the surface of the substrate. In another aspect of this embodiment, the cutting step includes: completely cutting through the top film layer and partially cutting through the operating agent layer. In another aspect of this embodiment, the operating agent comprises an adhesive. In yet another aspect of this embodiment, the providing step includes: coextruding the adhesive and a masking material, wherein the masking material is the top portion of the film structure. In another embodiment of the above method, the pressure is a finger or hand pressure.

In another embodiment of the above method, the cutting step includes: completely cutting through the top layer. In another embodiment of the above method, the cutting step includes: cutting in more than one direction. In another embodiment of the above method, the separable surface elements have at least a density of 400 elements per square inch before stretching. In one aspect of this embodiment, the separable surface elements have at least a density of 2500 elements per square inch before stretching. In another aspect of this embodiment, the separable surface elements have at least a density of 10,000 elements per square inch before stretching. In another embodiment of the above method, the film structure is multilayered. In another aspect of this embodiment, the multilayer film structure is formed by coextrusion.

In another embodiment of the above method, the stretching step includes biaxially stretching the film structure. In another embodiment of the above method, the stretching step includes simultaneously biaxially stretching the film structure. In another embodiment of the above method, the stretching is inelastic stretching. Another embodiment of the present invention provides a film structure formed by the above method.

Another aspect of the present invention provides an alternative method of forming and applying a film structure having controllable surface contact properties. This method comprises: providing a film structure which has a first major surface and an intermediate layer between the top portion and the second major surface, a second major surface, a top portion under the first major surface, wherein the top portion includes a plurality of stems each defining a separable element; and inelastically stretching the film structure to separate the separable surface elements across the first major surface of the film structure and to increase the exposure of the intermediate layer surface of the film structure through spacings between adjacent separated separable surface elements; applying the first major surface of the film structure to a surface of a substrate; and applying pressure to the second major surface of the film such that the operating agent contacts the structure surface of the substrate.

One embodiment of the present invention further comprises: applying the first major surface of the film structure to a surface of a structure; and applying pressure to the second major surface of the film structure such that the intermediate layer contacts the surface of the substrate. In another embodiment of the above method, the exposed portions of the intermediate layer form a plurality of recesses, each recess having a recess face spaced from the first major surface and exposed through one of the spacings between adjacent and separated surface elements. In another embodiment of the above method, the film structure further includes an operating agent, which at least partially defines the intermediate surface of the film structure. In one aspect of this embodiment, the operating agent comprises an adhesive. In another aspect of this embodiment, the operating agent comprises an adhesive, and the providing step includes: coextruding the adhesive and a base material to form an adhesive layer and a continuous layer; and forming stems extending from the continuous layer. In another aspect of this embodiment, the stems are formed during the coextruding step. In yet another aspect of this embodiment, the stems extend above the adhesive layer with top ends of the stems substantially devoid of adhesive.

In another embodiment of the above method, the pressure is a finger or hand pressure. In another embodiment of the above method, the film structure includes a continuous base film layer defining the second major surface of the film structure. In yet another embodiment of the above method, the film structure is multilayered. In one aspect of this embodiment, the multilayer film structure is formed by coextrusion. In another embodiment of the above method, the stretching step includes biaxially stretching the film structure. In another embodiment of the above method, the stretching step includes simultaneously biaxially stretching the film structure. Another embodiment of the present invention provides a film structure formed by the above method.

Another aspect of the present invention provides yet another alternative method of forming a film structure having controllable surface contact properties. This method comprises: providing a multilayer film structure which has first and second major surfaces and which includes an operating agent therein, the operating agent being spaced from the first surface of the film structure by a top portion of the film structure, the top portion being defined by electrically nonconductive predetermined separable surface elements, and the first surface of the film structure being defined by a plane across the separable surface elements; and stretching the multilayer film structure to separate the separable surface elements across the first surface of the film structure and to increase the exposure of the operating agent through spacings between adjacent separated separable surface elements.

One embodiment of the above method further comprises: applying the first major surface of the film structure to a surface of a substrate; and applying pressure to the second major surface of the film structure such that the operating agent contacts the surface of the substrate. In another embodiment of the above method, the operating agent comprises an adhesive. In another embodiment of the above method, the top portion of the multilayer film structure comprises a layer of particles, each particle defining one of the separable surface elements. In yet another embodiment of the above method, the film structure has a top film layer, and where said method further comprises: defining the separable surface elements by at least partially cutting the top film layer. In another embodiment of the above method, the providing step includes: forming a plurality of stems extending from a continuous portion of the film structure, each stem comprising one of the separable surface elements; and wherein the stretching step includes inelastically stretching. In another embodiment of the above method, the method further comprises the steps of: applying the first major surface of the film structure to a surface of a substrate; and applying pressure to the second major surface of the film such that the operating agent contacts the structure surface of the substrate. Another embodiment of the present invention provides a film structure formed by the above method.

BRIEF DESCRIPTION OF THE DRAWINGS

The present invention will be further explained with reference to the appended Figures, wherein like structure is referred to by like numerals throughout the several views, and wherein.

DETAILED DESCRIPTION OF THE INVENTION

Figure 1:
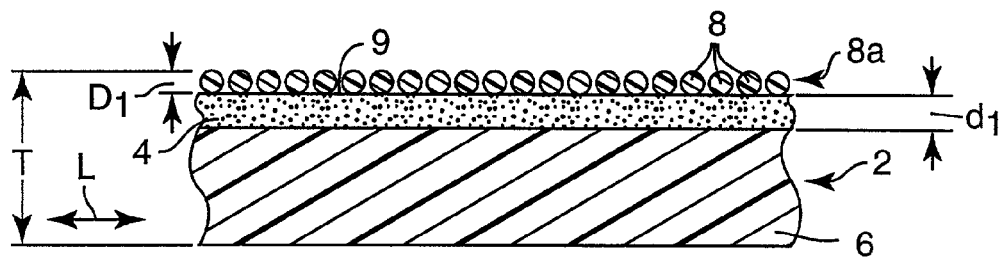
FIG. 1 is a side sectional view of a film structure according to a first embodiment of the inventive method before the film structure is stretched.

The present invention concerns methods for making film structures having controllable surface contact properties and such film structures. To make such film, a multilayer film assembly is formed using a suitable method (such as conventional coextrusion or lamination). The multilayer film assembly has an intermediate surface which may include an operating agent, such as an adhesive, preferably in a layer form. The multilayer film assembly may also include a base layer. The multilayer film assembly further has a top portion at least partially masking the intermediate surface (and the operating agent thereof if included). The top portion comprises a plurality of predetermined separable surface elements. For example, the top portion may be a masking layer such as a monolayer of discrete particles, a scored or cut continuous film layer, or a stemmed web.

After formation, the multilayer film assembly is stretched to separate the plurality of predetermined separable surface elements contained in the top portion and at least partially expose and/or increase the degree of exposure of the intermediate surface (and the operating agent thereof if included) through openings, recesses or lands between the separated surface elements such that the resultant multilayer film assembly has an activatable surface contact property whereby when the first major surface of the multilayer film assembly is applied to a surface of the substrate, the intermediate surface and/or operating agent thereof exhibits noticeably greater contact with the surface of the substrate after the multilayer film assembly is activated than before.

For the types of applications envisioned by the present invention, the activation of the activatable surface contact property is accomplished by applying pressure, for example finger or hand pressure or its equivalent, on the second major surface of the multilayer film assembly. In this disclosure, a finger pressure or a hand pressure refers to the kind of pressure an average user would normally apply using his/her finger or hand when trying to adhere an adhesive film to a substrate. However, any pressure that successfully activates the activatable surface contact property is suitable.

For the types of applications envisioned by the present invention, preferably the separated surface elements at least partially maintain their relative separation and the openings there between for an effective period of time (e.g., several hours or longer) without assistance of an external force. In other words, preferably the separated surface elements do not rejoin to their original position before the film structure was stretched.

As used in the present invention, the primary function of the stretching process is to generate a desired surface feature that has a controllable surface contact property. To accomplish that, a top portion comprising a plurality of separable surface elements is used. The separable surface elements are then separated by stretching the film assembly to achieve a desired topographical pattern. The technique makes the surface feature of the final film product predictable and easy to control.

Typically, the film assembly is stretched equally along two mutually perpendicular directions (i.e., biaxial stretching) to separate the surface elements in the plane of the film. However, the film assembly may be stretched along one, or more than two directions, and to unequal extents in either direction, depending on the specific performance desired in the final film structure. When stretched in more than one direction, stretching in different directions may be carried out either simultaneously or sequentially. Furthermore, the film assembly may be stretched with interspersed operations. For example, the film may be stretched in one or more directions, then treated with a desirable treatment (such as heating, annealing or simply waiting), and then stretched again either in the same direction or in a different direction. In essence, any manner of stretching may be used as long as it helps to create a desirable separation of the separable surface elements as described herein. Generally, a stretch ratio of at least 1:1.05 is expected. In this disclosure, a stretch ratio of 1:X represents an amount of stretching in a certain direction where the final film length in that direction is "X" times its original length in the same direction.

Attempts in the prior art to produce similar topographical features in adhesive films include those based on: 1) coating adhesives into recesses of a textured film; 2) embossing or printing non-adhesive projections over an adhesive film; and 3) randomly breaking up a disruptable thin top layer by deformation (see e.g., U.S. Pat. No. 5,948,493 to Groeger).

Among the above listed prior art methods, the coating method has disadvantage of being a two-step process, and further involves rheology control of adhesive. The printing method also has a disadvantage of being a two-step process. The third method results in uncontrolled feature size and surface geometry (i.e., the size and geometry of the broken apart surface elements are random by nature) and limited topographical relief by the top portion because the top portion is usually required to be very thin.

In comparison, the inventive method of stretching a film assembly having separable surface elements has several advantages, as discussed below.

As previously discussed, the primary function of the stretching process in accordance with the present invention is to provide a method to obtain a certain controllable surface contact property. The stretching process, however, brings certain additional benefits. For example, the stretching process according to the inventive method can be implemented in-line with conventional film-making equipment, and can therefore be accomplished in an integrated process and offers thin film capability. Since thin webs are usually difficult to manufacture (such as by casting, for example), it is more efficient to first form a thick web, then stretch the thick web and attenuate it to a desired final film thickness. Using the technique in accordance with the present invention, films that are less than 2 mil (0.0508 mm) thick, but still have a desired surface contact feature, can be made. It is further possible to make films that are less than 0.5 mil (0.0127 mm) thick, but still have a desired surface contact feature.

Another additional advantage of incorporating the technique in-line with film lines is lower cost of production. The film manufacturing lines as used according to the present disclosure can be substantially faster than typical web casting and forming operations. Furthermore, film manufacturing lines in this disclosure can produce wider output rolls than most cast processes.

In addition, biaxial film stretching may be carried out using standard film production equipment. Both cast-tentered process and blown-film process are viable means for this purpose. Cast-tentered films may be made sequentially (i.e., stretching in the machine direction followed by transverse stretching in a tenter), or simultaneously (i.e., using a simultaneous tenter). Either mechanical or electromechanical tenters may be employed towards this end.

Various techniques known in the art, such as solvent casting, lamination, or coextrusion, can be used to form a multilayer construction. If the multilayer construction is made by coextrusion and/or thermal lamination, the individual layers need to be amenable to being processed in a molten state.

In this disclosure, film structures having an adhesive as an operating agent are used as a primary example for purpose of illustration. Various types of adhesives known in the art, including common pressure sensitive adhesives, can be used.

The invention disclosed herein, however, is equally applicable to film structures containing other operating agents, such as chemicals, drugs, or even microelectronic elements. Suitable operating agents include, but are not limited to, cleansing agents, medicinal agents, emollients, lubricants, colorants, preservatives, protectants, condiments, fragrances, antiperspirants, and deodorants. The operating agent as applied in the final film structure may be in a continuous layer form, interconnected patches, or discrete pieces. In addition, a combination of more than one type of operating agents may be used. For example, a nonadhesive operating agent such as a chemical may be placed on top of an adhesive. In another form of combination, two or more operating agents may be blended together.

In addition to using an operating agent other than an adhesive, a textured film with no operating agent may also be made using the method of this invention for certain purposes. For instance, a film with stretched and textured recesses on a surface can be used as a food wrap that has no adhesion but allows for good air bleed through the recesses to prevent freezer burn. To make such a film, either a single layer or multiple layer precursor web can be scored or cut to an appropriate depth for desired textures. Other uses for a protective wrap which allows some limited or controlled bleed of air/moisture, etc., in or out of an opening or enclosure covered by the wrap are possible with the inventive film structure.

Based on the separable surface elements used and the methods of making thereof, three preferred types of embodiments of the film production methods are disclosed herein. In contrast to U.S. Pat. No. 5,948,493 to Groeger in which a disruptable thin top layer is randomly broken up by deformation, the three most preferred types of embodiments in accordance with the present invention have separable surface elements that are predetermined, separable along the predetermined boundaries thereof and subsequently separated by stretching.

Finally, various types of separable surface elements, including those known in the art, may be used in the top portion. Accordingly, various methods of making the separable surface elements known in the art may be used. Choice can be made with the benefits of all of the teachings herein and based on factors such as cost of production, equipment, and the types of intended applications of the product film.

First Embodiment

In a first embodiment, the separable surface elements comprise particles. The first embodiment is illustrated with reference to FIGS. 1, 2A, 2B, 2C and 7–10.

FIG. 1 shows a side sectional view of a film structure 2 prior to stretching according to an illustrative first embodiment of the inventive method. The film structure 2 has a first dimension (width—extending perpendicular to the page of FIG. 1), a second dimension (length—as illustrated by L in FIG. 1) and a third dimension (thickness—as illustrated by T in FIG. 1), wherein the first and the second dimensions are preferably much greater than the third dimension. The particular film structure 2 shown in FIG. 1 has an adhesive layer 4 (acting as an operating agent). In one embodiment, the film structure 2 may also have a stretchable base film 6. A plurality of non-adhesive particles 8 are placed on an exposed intermediate surface 9 (top side of the adhesive layer 4 as shown) and adhered thereto by the adhesive properties of the adhesive layer 4. For maximum control over the separation of the particles 8 by stretching, particles 8 are preferably, although not required to be, in a closely packed arrangement to each other.

The word "particles" encompasses materials in a powder, fiber or granular form. There are no specific restrictions on the size, or shape of the particles employed, although in general, the size needs to be large enough to rise above the surface of the operating layer in the finished film. Non-circular particles, fiber-like (elongated) particles, solid or hollow particles, metallic, inorganic, organic, ceramic, organic or polymeric particles may be employed depending on the temperature during processing, and the desired performance in the final film.

In addition, although particles 8 as shown in FIG. 1 are substantially spherical, uniform in size (with a diameter $D_1$), evenly distributed on the surface 9 and form a monolayer 8$a$, such a selection of particles 8 and distribution thereof is not required. Particles of any shape can be used, as long as they have a required dimension (height) $D_1$ in the thickness direction T of the film structure 2. Mixtures of populations of particles with differing average size, or populations with a distribution of particle sizes may also be employed to obtain specific performance in the finished film. It is also possible to have multiple applications of various particle populations. For instance, a large-particle population may be applied first to define a monolayer, after which a small-particle population may be applied to fill the interstices of the initial particle layer resulting in a consistent, coordinated arrangement of both populations. Such schemes could be performed multiple times with appropriate sized of particles and with interspersed stretching operations.

Figure 2A:
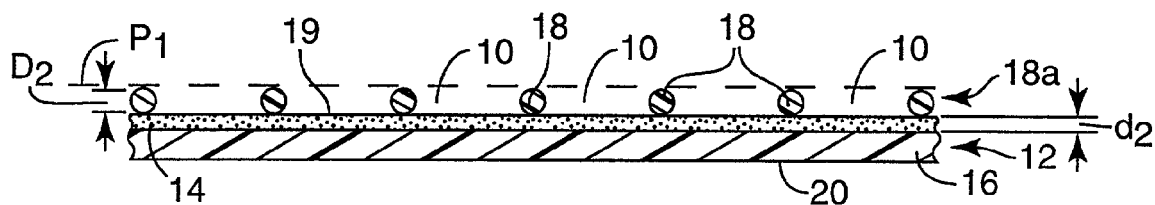
FIG. 2A is a side sectional view of a film structure according to the first embodiment of the inventive method after the film structure is stretched.
Figure 2B:
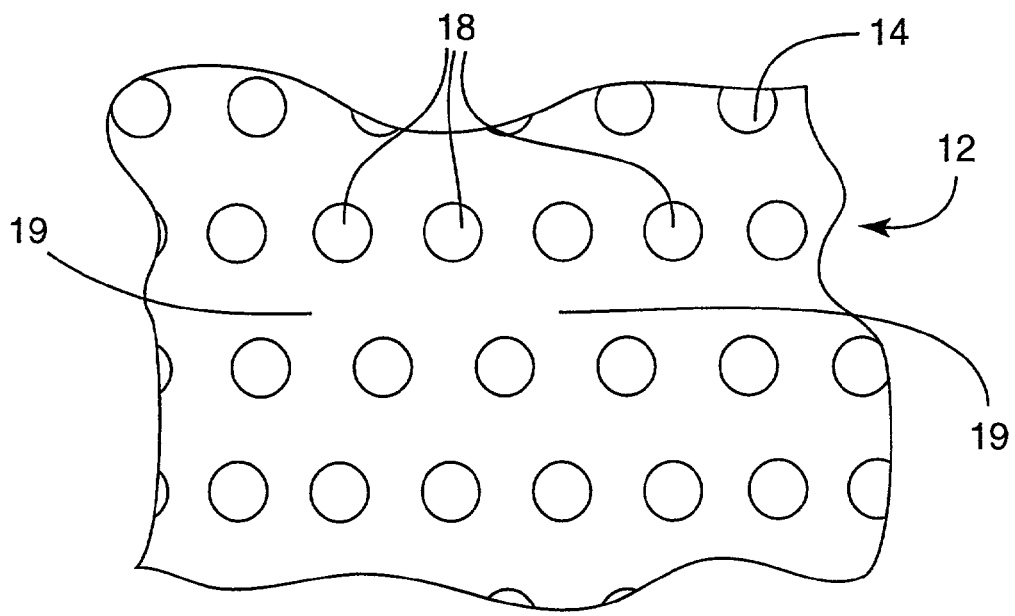
FIG. 2B is a schematic top view of a film structure according to the first embodiment of the present invention after the film structure is stretched.
Figure 2C:
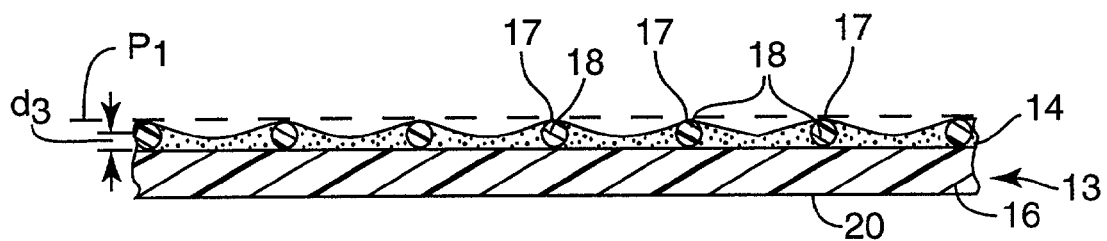
FIG. 2C is a side sectional view of a film structure according to an alternative version of the first embodiment of the inventive method (wherein particles are incorporated within the operating agent) after the film structure is stretched.

FIGS. 2A and 2B show a film structure 12 formed from stretching the film structure 2, preferably in both the first and the second dimensions of the film along its width and length (although stretching in just one direction may be sufficient, stretching in more than two directions may in some instances be desired).

The base layer 6 is stretched into a base layer 16. Particles 8 are separated from each other by stretching but remain effective as a monolayer 18*a*, thereby creating openings, recesses or lands 10 between particles 18. The adhesive layer 4 in FIG. 1 is stretched into an adhesive layer 14 in FIGS. 2A and 2B. A portion of intermediate surface 19 (the top surface of the adhesive layer 14 as shown) is thus exposed via the openings 10.

A plane $P_1$ (FIG. 2A) across the top of the monolayer 18*a* of particles 18 defines a first major surface of the film structure 12. If particles 18 have different sizes, the first major surface plane $P_1$ is approximately defined by a plane across the top of some of the largest particles 18. The first major surface $P_1$ is typically an application side of the film structure 12, meaning that this side of the film structure 12 is to be applied to a surface of a target object to obtain an intended effect, such as adhesion.

After stretching, the exposed portions of the adhesive layer 14 has an average thickness $d_2$ (FIG. 2A). Stretching of the film structure (2, 12) may or may not affect the size and shape of the particles 8/18, depending on the properties of the particles 8/18 and the temperature at which the stretching is carried out. Plastic particles, for example, tend to deform during stretching especially at high temperatures. Regardless of whether deformation of particles 8/18 occurs or what the degree of deformation is, the size of the particles after stretching (particles 18) is the basis for designing the film structure 12 such that in the stretched film structure 12 at least part of the adhesive 14 remain spaced from the first major surface $P_1$ of the film structure 12 by an effective distance due to the existence of particles 18. For purpose of illustration, in FIG. 2A, the adhesive 14 remains spaced from the first major surface $P_1$ of the film structure 12 by a distance roughly the same as the diameter (height) $D_2$ of particles 18, where $D_2$ is a variable if particles 18 have non-uniform sizes. When particles 18 are non-spherical, $D_2$ is equivalent to height of particles 18 in the thickness direction of the film structure 12. However, since the particles 18 may sink into the adhesive 14, in one embodiment, the height $D_2$ of at least some of the largest particles 18 is greater than the average thickness $d_2$ of the exposed portions of the adhesive layer 14 after stretching. This ensures that even if the particles 18 are buried in the adhesive layer 14, the exposed portions of the adhesive 14 remain spaced from the first major surface $P_1$ of the film structure 12 by an effective distance due to the existence of at least some of the largest particles 18. In still another embodiment, the height $D_2$ of at least some of the largest particles 18 is at least twice as the average thickness $d_2$ of the exposed portions of the adhesive layer 14 after stretching. This ensures that even if the particles 18 are buried in the adhesive layer 14, the exposed portions of the adhesive 14 remain spaced from the first major surface $P_1$ of the film structure 12 by a distance equal or greater than the average thickness $d_2$ of the exposed portions of the adhesive layer 14 due to the existence of at least some of the largest particles 18.

Stretching may be performed in an elastic or inelastic fashion. Stretching is preferably inelastic to at least partially maintain a certain degree of separation among the separated surface elements (particles 18) after stretching forces are removed from the film structure 12 and no other external force assisting the separation is present. In this disclosure, inelastic stretching is defined as stretching the film structure, in one or more directions, at least 5% from its initial state (1:1.05), with the final dimension(s) in the stretched film showing at least a permanent deformation of at least 5% (1:1.05) up to a permanent deformation of at least 50% of the imposed stretch (1:1.025). Stretching may be performed at room temperature or the film may be heated to facilitate deformation.

Figure 13:
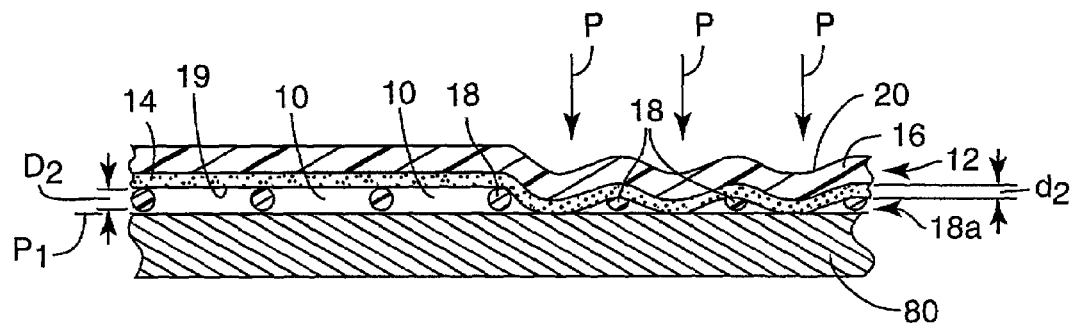
FIG. 13 is a side sectional view of the film structure of FIG. 2A applied to a substrate and illustrates pressure being applied to the film structure.

The resultant film structure 12 demonstrates a controllable surface contact property when the first major surface $P_1$ on the application side (the particle-bearing side) is applied to a surface of a target object. When the operating agent is an adhesive (adhesive layer 14), the film structure 12 demonstrates a tack-on-pressure property. Specifically, the film structure 12 shows a reduced tendency to cling prematurely to itself (and/or to a target surface) because of the existence of particles 18, but shows an increasing degree of adhesion when a proper pressure such as a finger pressure or a hand pressure is applied on a second major surface 20 of film structure 12 in a direction substantially transverse to the target surface, as illustrated in FIG. 13. The second major surface 20 is the back of the film structure 12 (e.g., on surface 20 of base layer 16).

The film structure 12 is particularly suitable for perishable food-wrapping applications, offering an advantage over the standard "cling" films in the market today for wrapping food (which have a high tendency to tangle). In addition to the tack-on-pressure feature, the adhesion performance characteristics of the inventive film structure may be adjusted based on the spacing between the particles 8, the size of the particles 8, holding power of the adhesive, thickness of the adhesive, and thickness and the stiffness of the base layer (or additional layers and materials which may comprise the base layer).

Particles 8 can be applied to the adhesive surface by flood coating the particles (for instance, using a fluidized-bed coater) prior to the stretching process. Excess particles 8 may be blown off the film web, or shaken off the web to obtain a monolayer of the particles 8 over the adhesive 4 in a consistent fashion. Standard film stretching equipment known in the art, such as length-orienters, tenters, etc., may be used to produce the stretched film 12.

In an alternative version of the first embodiment, the particles 8 can be incorporated in the operating layer 4 (e.g., adhesive 4) by blending the particles 8 into the operating layer 4 and subsequently making a multilayer film 2. In the case of an adhesive layer 4, for example, the particles 8 can be incorporated in the adhesive 4 by blending the particles into the adhesive and subsequently coextruding or coating the blend on a base material. In this case, particles made of materials with a high melting temperature may be necessary in order to maintain the particle shape through the extrusion process.

In this alternative version of the first embodiment, the coextruded film can then be stretched to obtain a similar film construction 13 (FIG. 2C) as described above. In the above alternative first embodiment (FIG. 2C), the operating layer 14 will tend to encapsulate the particles 18, but will generally be thinned out appreciably over the top surfaces 17 of the particles 18 if the effective or average thickness $d_3$ of the operating layer 14 in the final (stretched) film is smaller that the size of the particles 18. In the case of an adhesive (operating) layer 14, the thinned-out adhesive layer over the particles 18 will result in negligible adhesive holding power, and will result in repositionability of the final film 13. This may afford a more efficient process from a manufacturing viewpoint than having a separate particle coating operation.

The concept of using non-adhesive particles to detackify an adhesive surface is known in the art. U.S. Pat. No. 4,556,595 to Ochi, for example, discloses a pressure sensitive adhesive sheet structure having relocatable properties composed of a pressure sensitive adhesive layer and non-adhesive solid particles randomly but uniformly distributed over the surface of the adhesive layer. The Ochi patent, however, does not teach separating or spacing the particles in a manner as described herein.

The problem of spacing the particles has been addressed by several schemes in the past. These schemes include: 1) spraying/aspirating particles on an adhesive; 2) depositing solids from a liquid medium followed by a drying process; and 3) applying particles indirectly to a patterned liner and then laminating the liner to an adhesive. The prior art processes tend to be expensive, require special equipment and are difficult to manage in the way, which ensures consistency in the end product.

The technique in accordance with the present invention is an improvement over the prior art because the openings between adjacent particles 8 are controlled by the degree of stretch imposed on the film 2. By integrating the particle coating process with the process of making the film, high productivity and low costs can be achieved.

For the types of applications envisioned by the present invention, particles 8/18 do not need to be made of an electrically conductive material. In fact, in certain applications, it may be necessary or desirable that particles 8/18 be made of an electrically non-conductive material. On the other hand, different mechanical properties of particles 8/18 may be desirable for different applications and thus become an important factor that needs to be considered in choosing the material to fabricate particles 8/18.

Figure 7:
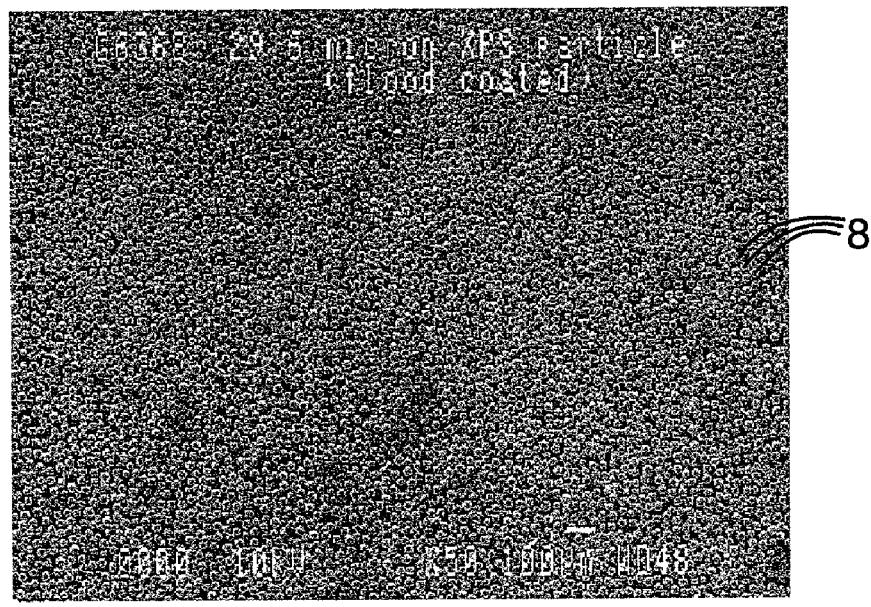
FIG. 7 is a scanning electron micrograph (×50) showing a top plan view of a film structure according to the first embodiment of the inventive method before the film structure is stretched.
Figure 8:
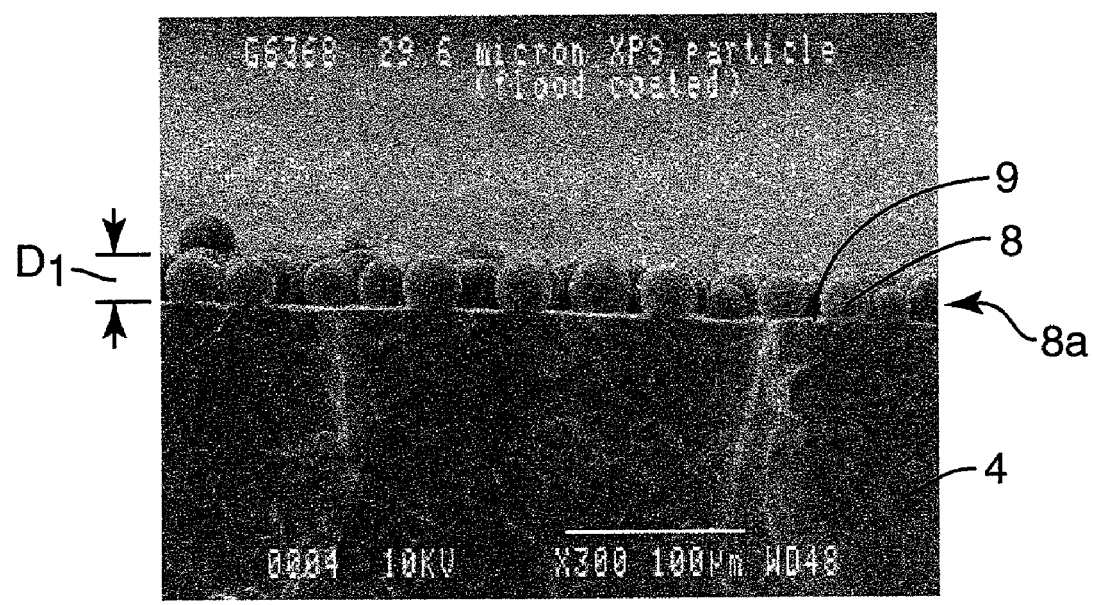
FIG. 8 is a scanning electron micrograph (×300) showing a side sectional view of a film structure according to the first embodiment of the inventive method before the film structure is stretched.
Figure 9:
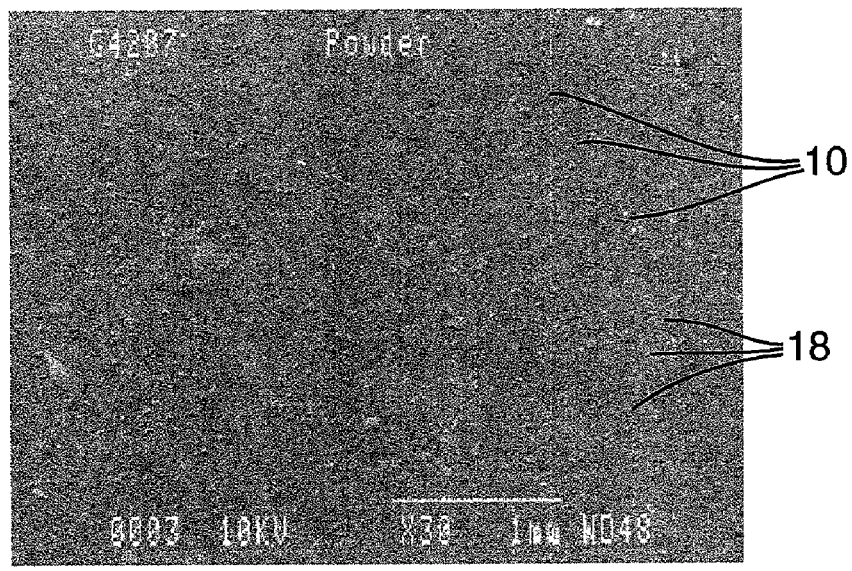
FIG. 9 is a scanning electron micrograph (×30) showing a top plan view of a film structure according to the first embodiment of the inventive method after the film structure is stretched.
Figure 10:
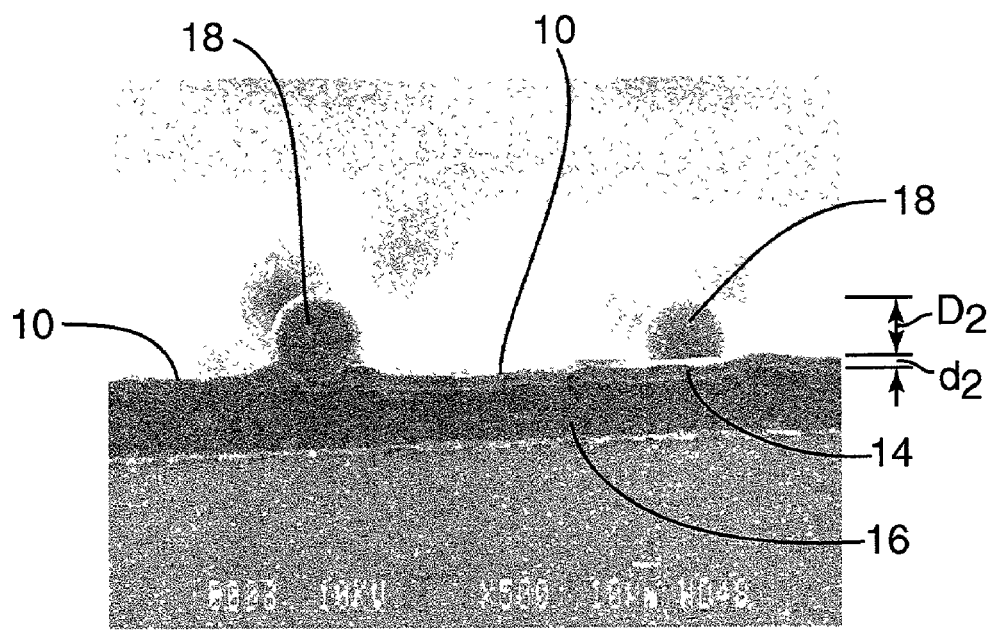
FIG. 10 is a scanning electron micrograph (×500) showing a side sectional view of a film structure according to the first embodiment of the inventive method after the film structure is stretched.

FIGS. 7–10 illustrate a preferred first embodiment of the film structure before and after it has been stretched. FIG. 7 is a scanning electron micrograph (×50) showing a top plan view of a film structure before the film structure is stretched. FIG. 8 is a scanning electron micrograph (×300) showing a side sectional view of a film structure before the film structure is stretched. FIG. 9 is a scanning electron micrograph (×30) showing a top plan view of a film structure after the film structure is stretched. FIG. 10 is a scanning electron micrograph (×500) showing a side sectional view of a film structure after the film structure is stretched.

Second Embodiment

In a second embodiment, the top portion containing separable surface elements comprises a scored or cut masking layer. By scored, it is meant any line of weakness of separation. The second embodiment is illustrated with reference to FIGS. 3, 4A, 4B, 11, and 12.

Figure 3:
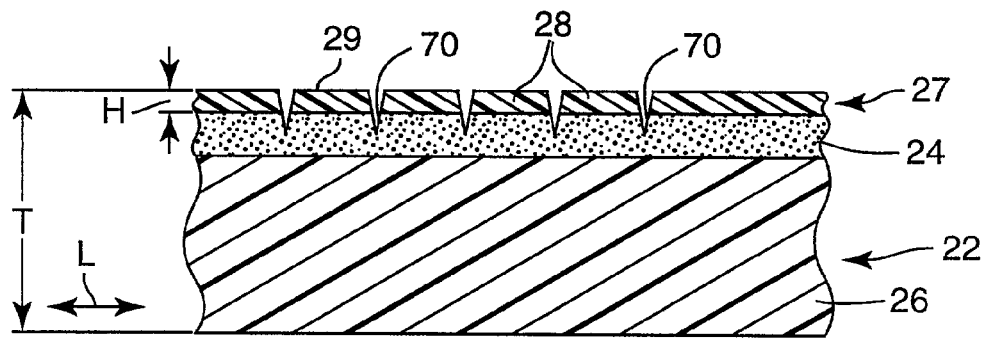
FIG. 3 is a side sectional view of a film structure according to a second embodiment of the inventive method before the film structure is stretched.

FIG. 3 shows a side sectional view of a film structure 22 prior to stretching according to an illustrative second embodiment of the inventive method. The film structure 22 has a first dimension (width—extending perpendicular to the page of FIG. 3), a second dimension (length—as illustrated by L in FIG. 3) and a third dimension (thickness—as illustrated by T in FIG. 3) wherein the first and the second dimensions are preferably much greater than the third dimension. The particular film structure 22 shown in FIG. 3 has an adhesive layer 24 (acting as an operating agent). In one embodiment, the film structure 22 may also have a stretchable base layer 26. A masking layer 27 is on top of the adhesive layer 24 and thus defines a first major surface 29 of the film structure 22. Preferably, the masking layer 27 has a substantially uniform thickness H, evenly spacing the adhesive layer 24 from first major surface 29 of the film structure 22.

As shown in FIG. 3, the masking layer 27 is scored or cut through from the top to form scores or cuts 70, preferably in a series of parallel lines (not shown) along the first and the second dimensions, so that the masking layer 27 is scored or cut into a grid of four-sided segments 28 such as squares, diamonds, rectangles or rhombuses, each segment being mechanically isolated from its neighbors. Each segment 28 therefore constitutes a separable surface element. However, there is no requirement for any particular manner or shape of scoring or cutting as long as the cutting generates desired separable surface elements 28 on the masking layer 27, although different cutting mechanisms may have different efficiency or productivity. A blade cutter was used in the examples described herein, but any conventional methods such as laser ablation or embossing may be used to sever the masking layer into separable surface elements. Furthermore, there is no requirement for any particular shape or relative sizes of the separable surface elements 28 as long as the final film structure (stretched film) has the desired surface contact properties. In general, each separable surface element 28 resulting from cutting has an n-sided polygon shaped top side.

For the applications envisioned with the present invention, it is desired that separable surface elements 28 have a density, before stretching, of greater than 100 elements per square inch (15.5 elements per square centimeter), preferably 1000 elements per square inch (155 elements per square centimeter), more preferably 2500 elements per square inch (388 elements per square centimeter) before stretching, and still more preferably 10,000 elements per square inch (1550 elements per square centimeter). It is contemplated that a density of the separable surface elements prior to stretching as high as 40,000 elements per square inch (6200 elements per square centimeter) is possible.

Preferably (as shown in FIG. 3), the masking layer 27 is completely cut through while the adhesive layer 24 is partially cut through, although it may be sufficient that the scoring merely weaken or only partially sever the thickness of the masking layer 27 in some manner in order to achieve the desired separation effect. In the embodiment where a stretchable base layer 26 is used, it is preferred that multi layer film structure 22 be formed before cutting of the masking layer 27. Although it is possible that the masking layer 27, either alone or together with the operating agent (adhesive layer) 24, is scored or cut first and then laminated together with the base layer 26.

In either of the above situations and unlike that in the first embodiment (particles), the separable surface elements 28 are formed directly on a continuous portion of the film structure 22 instead of being incorporated into the film structure as pre-formed discrete pieces as in the case of particles. Here, "a continuous portion of the film structure" refers to one or more of the following depending on the embodiment: the base layer 26, an uncut portion of the adhesive layer 24, or an uncut portion of the masking layer 27.

Figure 4A:
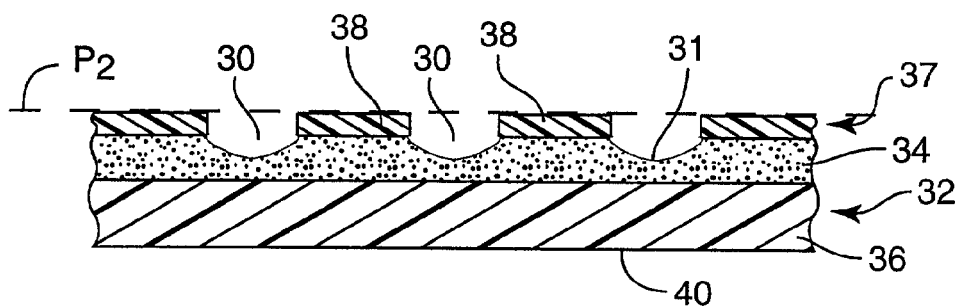
FIG. 4A is a side sectional view of a film structure according to the second embodiment of the inventive method after the film structure is stretched.
Figure 4B:
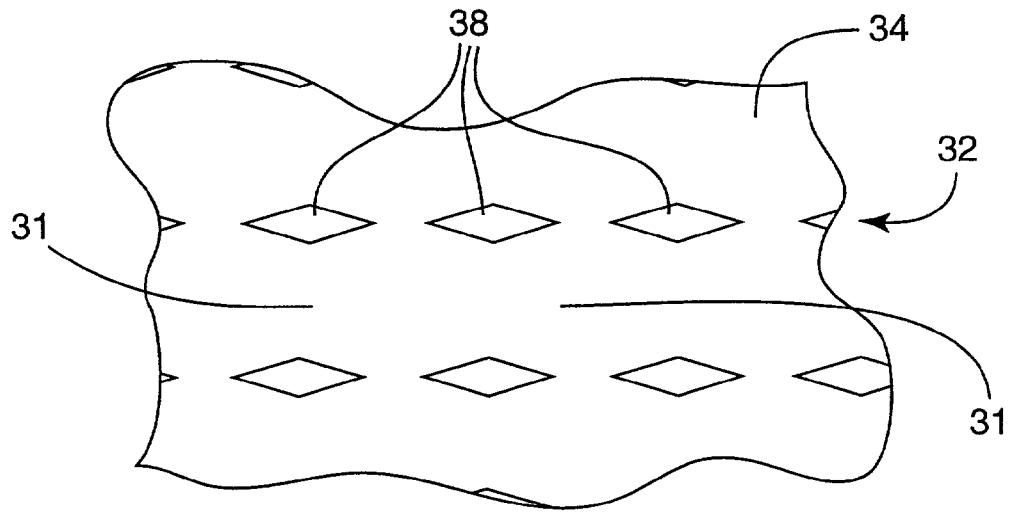
FIG. 4B is a schematic top view of a film structure according to the second embodiment of the inventive method after the film structure is stretched.

FIGS. 4A and 4B show a film structure 32 formed from stretching the film structure 22, preferably in both the first and the second dimensions of the film. (Again, stretching in just one direction, or more than two directions, may be desired in some instances.) Base layer 36 in FIG. 4A is a result of stretching the base layer 26 in FIG. 3. Adhesive layer 34 is a result of stretching the adhesive layer 24 in FIG. 3. Segments 38 of the masking layer (27, 37) also stretch out and become separated from each other by the stretching, thereby creating openings, recesses or lands 30 between segments 38, yet still serving to some degree as a masking layer 37 for the adhesive layer 34. The openings (recesses or lands) 30 facilitate at least a partial exposure or increased exposure of portions of intermediate surface 31, which is a portion of upper surface of the adhesive layer 34 as shown, but may be just a face of recess 30 when no operating agent is used. Stretching may result in a reduction of thickness of the surface segments.

A plane $P_2$ (FIG. 4A) across the top of the masking layer 37 defines a first major surface of the film structure 32. The exposed intermediate surface portions 31 of the adhesive layer 34 are spaced from the plane $P_2$ by the segments 38 with a distance at least the same as the thickness of the segments 38, which may or may not remain the same as the thickness H of original segments 28. The first major surface is typically an application side of the film structure 32, meaning that this surface or side of the film structure 32 is to be applied to a surface of a target object to obtain an intended effect, such as adhesion.

Figure 14:
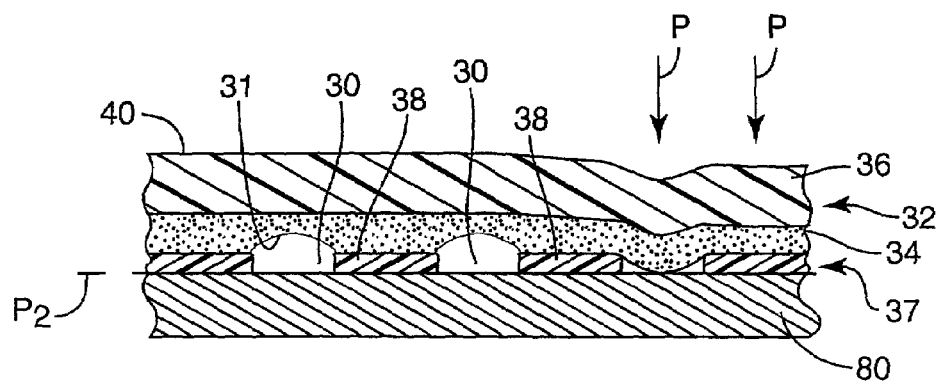
FIG. 14 is a side sectional view of the film structure of FIG. 4A applied to a substrate and illustrates pressure being applied to the film structure.

The resultant film structure 32 has a controllable surface contact property such as adhesion performance similar to that of the film structure 12 illustrated in the first embodiment. The film structure 32 has islands of non-adhesive protrusions (segments 38) that protect an operating agent (adhesive layer 34) from premature contact with a target surface. The operating agent can then be contacted against the target surface by application of pressure on the backside 40 of the film structure 32, as illustrated in FIG. 14.

As in the first embodiment, other types of operating agents may also be used. In addition, a textured film with no operating agent may also be made using the method of this invention for certain purposes. For instance, a film 32 with stretched and textured recesses 30 on the application side $P_1$ but containing no adhesive 34 can be used as a food wrap that has no adhesion but allows for good air bleed through the recesses to prevent freezer burn.

Variations of the scoring or cutting the masking layer 27 may be used by one skilled in the art. For example, cutting may be performed using a variety of schemes. Instead of using a cutter as described above, alternate cutting or surface weakening schemes such as a water-jet, laser-beam, rotary-die, or embossing roll may be used. In general, water-jets and laser-beams may result in a wider cut swath than a cutter. Further, water-jets and laser-beams are best suited when the cutting direction is along the machine direction. One advantage with a laser beam is that intricate patterns such as waves, squiggles, predefined contours, etc. can be accomplished by programming the path into the laser scanning device. It is also envisioned that in certain situations (e.g., by using a brittle top layer), cutting can be effectively performed using an embossing roll.

The size and geometry of the islands, such as diamonds, squares, rectangles, or any general parallelograms, can be varied based on cutting at various angles and at various cutting spacings. The spacing can be controlled by the relative speed of the web, and the speed of the cutting device. With the materials in the second embodiment example below, the minimum distance along the machine direction that resulted in good separation of the diamonds was about 250 microns ($\mu$m). When the cuts were made closer there was an increased risk of the top polyethylene layer delaminating from the adhesive, and subsequently not separating into islands but instead forming clusters of diamonds due to this delamination. By using alternate materials, such as using a top layer material that has a higher bond strength to the adhesive layer, closer cuts would be possible.

It is also possible to have cuts only in one direction, whereby a ribbed pattern can be formed in the final film. Tandem cutting is possible where multiple cuts are made along parallel directions using multiple cutting stations in order to obtain smaller cut spacing than would be possible with just a single cut in that direction. Multiple cuttings at multiple angles would result in other shapes such as triangles and other polygons. It is, therefore, possible to achieve a wide variety of controllable shapes and sizes of the topographical features or the separable surface elements.

Figure 11:
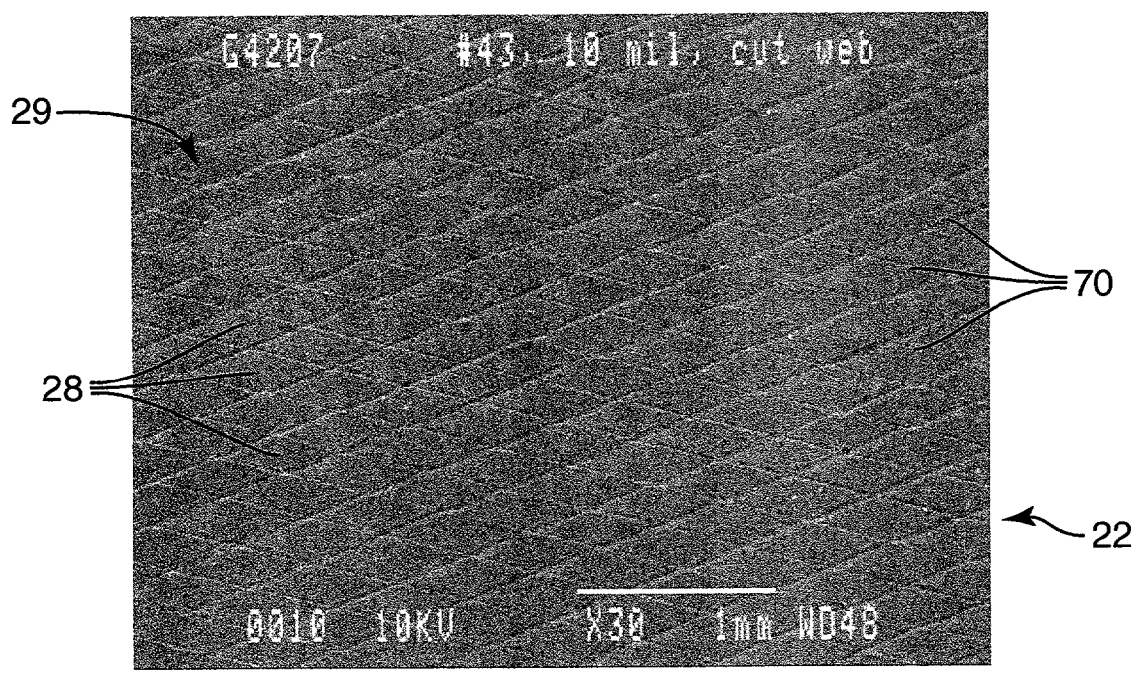
FIG. 11 is a scanning electron micrograph (×30) showing a top plan view of a film structure according to the second embodiment of the inventive method before the film structure is stretched.
Figure 12:
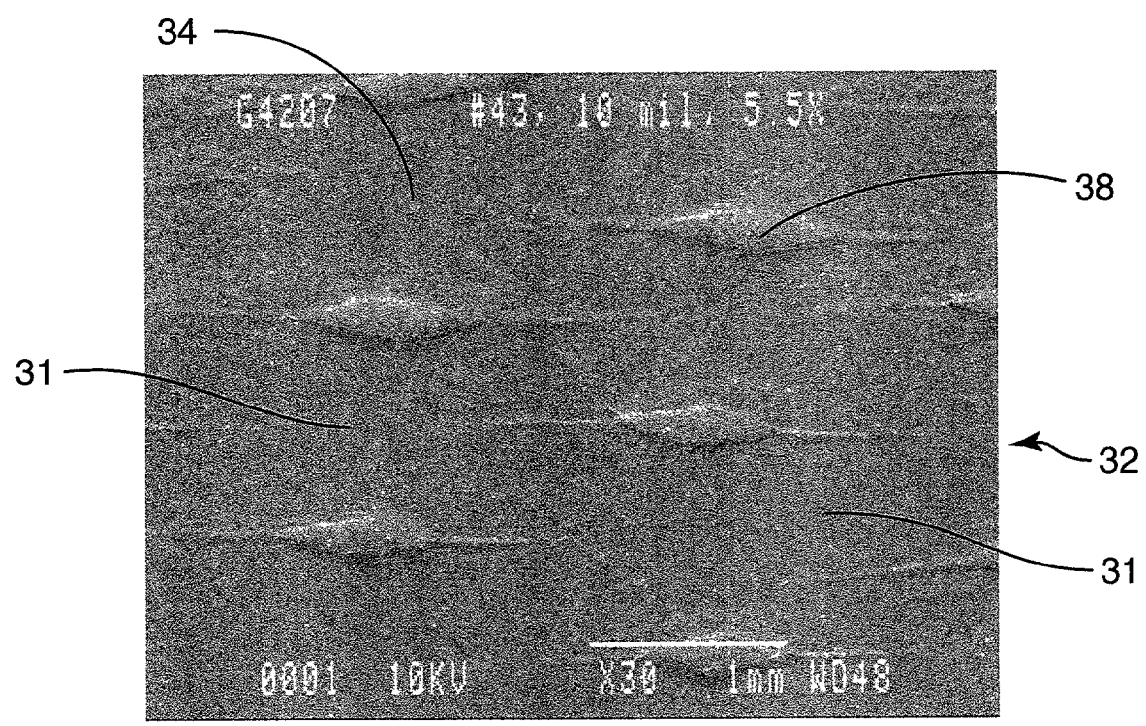
FIG. 12 is a scanning electron micrograph (×30) showing a top plan view of a film structure according to the second embodiment of the inventive method after the film structure is stretched.

FIGS. 11 and 12 illustrate a preferred second embodiment of the film structure. FIG. 11 is a scanning electron micrograph (×30) showing a top plan view of a film structure before the film structure is stretched. FIG. 12 is a scanning electron micrograph (×30) showing a top plan view of a film structure after the film structure is stretched.

Third Embodiment

In a third embodiment, the top portion containing separable surface elements comprises stems of a stemmed-web film. The third embodiment is illustrated herein with reference to FIGS. 5, 6A and 6B.

Figure 5:
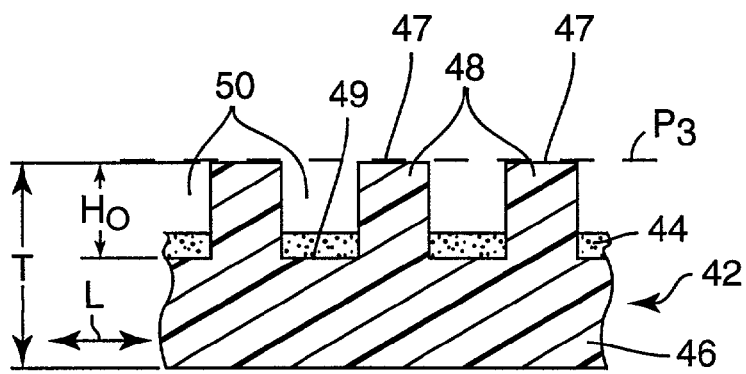
FIG. 5 is a side sectional view of a film structure according to a third embodiment of the inventive method before the film structure is stretched.

FIG. 5 shows a side sectional view of a etching film structure 42 prior to stretching according to an illustrative third embodiment of the inventive method. The film structure 42 has a first dimension (width—extending perpendicular to the page of FIG. 5), a second dimension (length—as illustrated by L in FIG. 5) and a third dimension (thickness—as illustrated by T in FIG. 5) wherein the first and the second dimensions are preferably much greater than the third dimension.

The film structure 42 has a stretchable base layer 46 from which a plurality of stems 48 extend. Although the stems 48 can be separately formed, they are preferably formed as an integral part of the base layer 46. For example, a stemmed web film structure 42 with stems 48 extending from a base layer 46 and above an adhesive layer 44 can be cast by coextruding the adhesive and the base layer simultaneously using a microstructured tool. One suitable method used to extrude the stemmed web film structure 42 is described in detail in U.S. Pat. No. 6,106,922, co-owned by the assignee of the present application, which is hereby incorporated by reference. It is preferred that the top ends 47 of the stems 48 be essentially devoid of adhesive 44. To this end, the material rheology and other process conditions are closely controlled to have the base layer 46 puncture through the adhesive layer 44 during the process forming stems 48. In general, low viscosity base layer resins resulted in better puncturing-through of the stems through adhesive layer 44, with the stem tips 47 being essentially devoid of the adhesive 44 or have no adhesive on them. It was found that a material having a melt flow index (mfi) greater than 50 is preferred when used as a base layer 46.

The stems 48 are preferably separate from each other and leave openings, recesses or lands 50 between them. The stems can have any desired shape, such as cylindrical, tapered, conical, square in section, etc. An operating agent 44 is disposed on intermediate surface 49 (non-stemmed top surface of the base layer 46 as shown) at opening 50. The particular film structure 42 shown in FIG. 5 has an adhesive layer 44 (acting as an operating agent). The adhesive of the adhesive layer 44 at one opening 50 may be separate from the adhesive at another opening 50, but preferably all of the adhesive is deposited over the surface 49 of the base layer 46 as a connected layer (the stems 48 are thus like islands among the adhesive layer 44).

A first major surface of the film structure 42 is defined by the tops of the stems 48, as illustrated by plane $P_3$ in FIG. 5. Preferably, the stems 48 have a substantially uniform height $H_O$ that is greater than the thickness of the adhesive 44, thereby evenly spacing the adhesive layer 44 from the first major surface of the film structure 42.

Figure 6A:
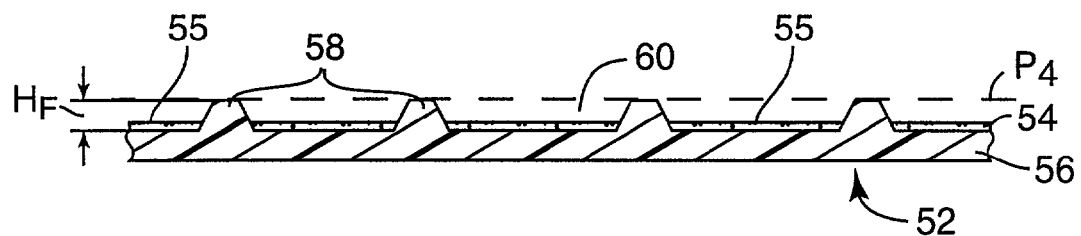
FIG. 6A is a side sectional view of a film structure according to the third embodiment of the inventive method after the film structure is stretched.
Figure 6B:
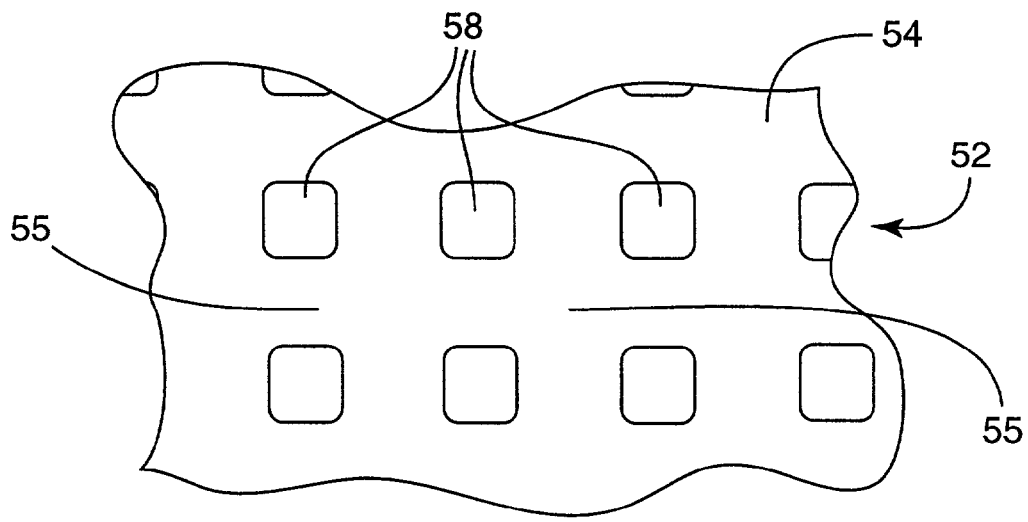
FIG. 6B is a schematic top view of a film structure according to the third embodiment of the inventive method after the film structure is stretched.

FIGS. 6A and 6B show a film structure 52 formed from inelastic stretching the film structure 42, preferably in both the first and the second dimensions of the film. Stems 58 in FIG. 6A are the result of stretching the stems 48 in FIG. 5. As a result of the stretching, the stems 58 are shorter and further apart from each other, thereby increasing the size of the openings, recesses or lands 60 between them. Although not required, adhesive layer 44 in FIG. 5 is preferably stretched along with the base layer 46 (which becomes base layer 56 in FIG. 6A after stretching). Adhesive layer 54 in FIG. 6A is the result of stretching the adhesive layer 44 in FIG. 5. The openings (recesses or lands) 60 facilitate at least a partial exposure of portions of intermediate surface 55, which is a portion of upper surface of the adhesive layer 54 as shown, but may be just a face of recess 60 when no operating agent is used. The first major surface of the film structure 52 is still defined by the tops of the stems 58, as illustrated by plane $P_4$ in FIG. 6A. Furthermore, the height of the stems 58 is reduced from $H_O$ to $H_F$ by stretching. Preferably, $H_F$ is still greater than the thickness of the adhesive layer 54, thereby spacing the adhesive layer 54 from the first major surface of the film structure 52.

The plane across the top of the stems 58 (plane $P_4$) defines a first major surface of the film structure 52. The first major surface is typically an application side of the film structure 52, meaning that this surface or side of the film structure 52 is to be applied to a surface of a target object to obtain an intended effect, such as adhesion.

Figure 15:
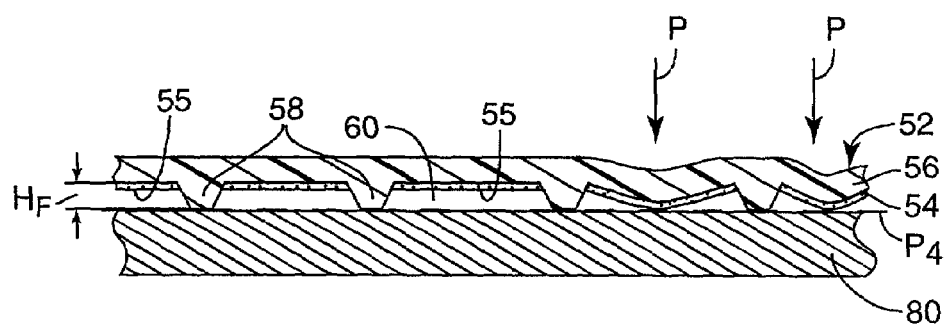
FIG. 15 is a side sectional view of the film structure of FIG. 6A applied to a substrate and illustrates pressure being applied to the film structure.

The resultant film structure 52 has controllable surface contact property such as adhesion performance similar to that of the film structures 12 and 32 illustrated in the first embodiment and the second embodiment, respectively. The film structure 52 has islands of non-adhesive protrusions (stems 58) that protect an operating agent (adhesive layer 54) from premature contact with a target surface. The operating agent can thus be selectively contacted against the target surface by application of a proper pressure such as a finger or hand pressure, as illustrated in FIG. 15.

Similar to that disclosed in the second embodiment (cut film), a textured film with no operating agent may also be made using the method in accordance with the third embodiment for certain purposes. For instance, a film 52 with stretched and textured recesses 60 on the application side $P_4$ but containing no adhesive 54 can be used as a food wrap that has no adhesion but allows for good air bleed through the recesses to prevent freezer burn.

FIG. 13 illustrates the film structure 12 of the first embodiment in contact with the surface of a substrate 80. The first major surface $P_1$ of the film structure 12 is in contact with the first surface of the substrate. When pressure (designated by arrows and reference P on the right-hand side of the Figure) is applied to the second major surface 20 of the film structure 12, the operating agent (adhesive layer 4) contacts the surface of the substrate 80. As the pressure P is applied, the film structure is deformed to place the operating agent in contact with the surface of the substrate. Where pressure P is not applied (on the left-hand side of the Figure), the operating agent is not in contact with the surface of the substrate 80. The particles 18 keep the operating agent (adhesive layer 4) away from or out of contact with the substrate 80, until pressure is applied to place the operating agent (adhesive layer 4) into contact with the substrate 80.

FIG. 14 illustrates the film structure 32 of the second embodiment in contact with the surface of a substrate 80. The first major surface $P_2$ of the film structure 32 is in contact with the first surface of the substrate. When pressure (designated by arrows and reference P on the right-hand side of the Figure) is applied to the second major surface 40 of the film structure 32, the operating agent (adhesive layer 34) contacts the surface of the substrate 80. As the pressure P is applied, the film structure 32 is deformed to place the operating agent (adhesive layer 34) in contact with the surface of the substrate. Where pressure P is not applied (on the left-hand side of the Figure), the operating agent is not in contact with the surface of the substrate 80. The segments of the masking layer 38 keep the operating agent (adhesive layer 34) away from or out of contact with the substrate 80, until pressure is applied to place the operating agent (adhesive layer 34) into contact with the substrate 80.

FIG. 15 illustrates the film structure 52 of the third embodiment in contact with the surface of a substrate 80. The first major surface $P_4$ of the film structure 52 is in contact with the first surface of the substrate. When pressure (designated by arrows and reference P on the right-hand side of the Figure) is applied to the second major surface of the film structure 52, the operating agent (adhesive layer 54) contacts the surface of the substrate 80. As the pressure P is applied, the film structure 52 is deformed to place the operating agent (adhesive layer 54) in contact with the surface of the substrate. Where pressure P is not applied (on the left-hand side of the Figure), the operating agent is not in contact with the surface of the substrate 80. The stems 58 keep the operating agent (adhesive layer 54) away from or out of contact with the substrate 80, until pressure is applied to place the operating agent (adhesive layer 54) into contact with the substrate 80.

Summary of the Embodiments

In all three (first, second and third) types of embodiments, the separable surface elements are made in a predetermined and controllable manner. In the first embodiment, the separable surface elements are formed from pre-formed discrete particles. With the second and third embodiments, however, the separable surface elements are further formed directly on (the second embodiment) or out of (the third embodiment) a continuous portion of the film assembly without separately incorporating therein pre-formed discrete objects as separable surface elements.

The extent of stretching dictates separation of the separable surface elements. For each choice of base and adhesive materials and stretch conditions such as temperature and stretch rate or stretch ratio, there will be an optimum range of stretch ratio. The preferred range of stretch ratios varies, among other factors, with the material used for the base layer (6, 16, 26, 36, 46 and 56).

Wider separations result in increased separations of the non-adhesive protrusions (separable surface elements). An optimum stretch ratio may be chosen based on the desired performance and the height of the protrusions.

Although simultaneous biaxial stretching is preferred for this application, various performance characteristics may be obtained by other stretching schemes, including uniaxial, asymmetric biaxial, sequential biaxial, simultaneous biaxial stretching, etc.

Additionally, although the above described process is best suited for a cast stretch film process, blown film processes may also be employed.

Furthermore, variations of the multi-layer web described in the above examples can offer additional performance characteristics. For instance, additional layer or layers with an anti-block additive can be included to reduce the inherent cling in the base polyethylene layer. For food wrap applications, the top layer could be a pigmented layer, such as $TiO_2$, which could potentially offer cosmetic and seal indicating properties.

Although in the first embodiment, an adhesive is required to adhere the particles, an operating agent other than an adhesive may be used in addition to the adhesive. Furthermore, with the second and the third types of embodiments, alternate constructions can be made without the adhesive functionality, that is, a nonadhesive operating agent may be used in place of the adhesive.

In addition, the surface contact properties can be adjusted by employing a desired rigidity of the surface elements. The rigidity of the surface elements can vary from being collapsible to rigid.

Depending on the spacing (size of opening) between the separable surface elements (such as particles, cut segments and stems), the size of the separable surface elements, the thickness and adhesion performance characteristics of the adhesive, and the stiffness and thickness of the film base, various other adhesion performances can be obtained.

The film structure described herein can be used for a variety of other purposes, depending on the type of operating agent used, multilayer structure, variations of separable surface elements, stretching scheme including the degree of stretching, etc. For example, a novel application of the film structure and the method of making disclosed in the present invention is described in a U.S. patent application entitled "Tack-on-pressure Films for Temporary Surface Protection and Surface Modification" (Ser. No. 10016541; co-assigned to the 3M Innovative Properties Company. The above-identified U.S. patent application, which is hereby incorporated by reference, discloses a method for temporary surface protection or surface modification using a sheet material, wherein a selectively activated adhesive is provided on one side of a three-dimensional sheet material, for maintaining the sheet material in place for uses such as the dental bib, tool tray liner, or to provide the desired optical effects on a surface to which the sheet material has been adhered.

The operation of the present invention will be further described with regard to the following detailed examples. These examples are offered to further illustrate the various specific and preferred embodiments and techniques. It should be understood, however, that many variations and modifications may be made while remaining within the scope of the present invention.

EXAMPLES OF THE FIRST EMBODIMENT

Example 1

As an example of the first embodiment described above, a prototype film structure was made by a process comprising the following steps: (1) Extrusion; (2) Lamination; (3) Flood Coating; and (4) Stretching. Details of the above process are described below.

1. Extrusion:

A base polyethylene layer was cast and a 125 mm×125 mm square piece (coupon) was cut from the cast sheet.

The polyethylene used was Mxten CM 27057-F from Eastman Chemicals Co., Kingsport, Tenn. The material is a linear low density polyethylene (LLDPE) resin with a density of 0.910 g/cc (0.910 g/ml) and melt flow index (mfi) of 2. The resin was extruded in a 1.75 inch (44.5 mm) screw HPM extruder (HPM Corp., Mt. Gilead, Ohio) at a melt temperature of 450° F. (232.2° C.). The molten sheet was cast onto a chilled steel roll at 125° F. (51.7° C.). The bottom section of the casting roll was immersed in water to enable heat transfer from the cast sheet. The thickness of the cast sheet was 1250 microns ($\mu$m).

2. Lamination:

A layer of an adhesive was laminated over the coupon. The hot-melt adhesive used was a commercial blend made by H. B. Fuller Company of St. Paul, Minn. (HL-2697PT). The adhesive was extruded at 400° F. (204.4° C.) using a 0.75 inch (19.05 mm) extruder and was sandwiched between two silicone-coated paper liners. The thickness of the adhesive was 313 microns ($\mu$m). A 101 mm×101 mm square of the adhesive (sandwiched between the liners) was cut. After removing one of the liners, the adhesive was transferred to the coupon. The second liner was subsequently removed.

Alternatively, the above extrusion and lamination steps may be replaced by a co-extrusion process in which a two-layer web including the adhesive layer and the base polyethylene layer is coextruded using a conventional extruding method.

3. Flood Coating:

Non-adhesive cross-linked polystyrene particles with an average diameter of a 29.6 microns ($\mu$m) were manually flood coated on the adhesive side of the laminated coupon. An excess of the above particles was poured on the adhesive surface. The coupon was manually tilted back and forth in order to expose the entire area of the adhesive to the particles. A fixed amount of the particles adhered to the adhesive, essentially producing a monolayer of the particles. The excess amount was removed by holding the coupon upside down and tapping the back of the sheet so that essentially a monolayer of the particles stayed on the adhesive in a consistent self-regulating manner. An average amount of 0.15 gm of the particles adhered to the adhesive. Excess particles (non-adhered particles) may also be blown off or vacuumed off the web in order to obtain a constant loading of the particles on the adhesive.

The particles were prepared by the limited coalescence suspension polymerization method as described in U.S. Pat. No. 5,238,736 (which is hereby incorporated by reference). The specific method used in the present example was as follows: Aqueous mixture of 2139 g deionized water, 15 g Ludox TM-50 colloidal silica (DuPont, Wilmington, Del.), 1.04 g of 50% solution of diethanolamine-adipic acid condensate (as promoter) and 0.48 g of potassium dichromate was stirred and adjusted to pH 4 by addition of 10% sulfuric acid. A monomer solution of 1440 g styrene (Dow Chemical Co., Midland, Mich.), 36 g divinyl benzene-HF (Dow Chemical Co.) and 2.1 g of VAZO 64 initiator (DuPont) was added to the above aqueous mixture, mixed well, and passed through a Manton-Gaulin Homogenizer Model #15 MR (APV Gaulin Corp., Wilmington, Mass.) at about 1000 psi for one minute, and recycled three times. The homogenized suspension was poured into a 5-liter split resin flask equipped with mechanical agitator, condenser and nitrogen inlet. The suspension was then heated to 70° C under nitrogen and kept for 24 hours to complete polymerization. The polymerized suspension was screened through a 40 mesh sieve, then filtered with #54 filter paper on a Buchner funnel and washed several times with water to give a wet cake containing polystyrene particles of about 30 $\mu$m. The wet cake was then dried at ambient temperature to give a free-flowing powder.

4. Stretching:

The sheet was stretched in a batch stretcher KARO IV Laboratory Stretcher (Bruckner, Siegsdorf, Germany). The stretch temperature was 244.4° F. (118° C.). The coupon was heated for 70 seconds, after which the coupon was stretched at a constant rate of 10% per second to a final stretch ratio of 1:7 in each direction. In the final stretched film, the polyethylene layer was about 22 microns ($\mu$m) thick, and the adhesive layer was about 5.5 microns ($\mu$m) thick.

Samples from the above sheet prototypes made in accordance with the above process were tested for their adhesion performance. The tests performed are described as follows.

Adhesive-To-Adhesive Test:

The non-adhesive side of a 1.5 inch (38.1 mm) wide strip of a sample inventive film was adhered to the test platen of a Slip/Peel Tester (Instrumentors Inc., Strongsville, Ohio) using a 2-sided transfer adhesive. The tester is used to measure the release force for high speed operation.

A 1 inch (25.4 mm) wide strip of the sample film was then laid over the 1.5 inch (38.1 mm) wide strip of sample inventive film (adhesive-side to adhesive-side) and rolled down with either a 200 gm roller or by applying finger pressure.

The samples were then tested in the Slip/peel tester to quantify the peel forces (at 90°, and at 12 inches (0.3 m) per minute).

Adhesive-To-Steel Test:

A 1 inch (25.4 mm) wide strip of the inventive sample film was laid over a clean stainless steel platen and rolled down with either a 200 gm roller, or by applying finger pressure, and tested with the slip/peel tester.

In addition to the inventive film, a removable office tape (referenced as Clear Scotch® Tape 811, available from Minnesota Mining and Manufacturing Company, St. Paul, Minn.) was also tested for comparison purposes. The methods used to test the comparison film (3M Clear Scotch® Tape 811) were identical to the method used to test the inventive film except that the width of the sample 3M removable office tape used in tests was 0.75 inches (19.05 mm) instead of 1 inch (25.4 mm). Correspondingly, the width of the transfer film used in the adhesive-to-adhesive test for the removable office tape sample was also 0.75 inches (19.05 mm) instead of 1 inch (25.4 mm). The test results are given below.

Peel Force Test Results

1) Particle-coated film (1 inch), average of two specimens (in grams):

TABLE 1

| Roller | adhesive-to-adhesive | | | adhesive-to-steel | | |
|---|---|---|---|---|---|---|
| | Average | High | Low | Average | High | Low |
| 200 gm roller | 9 | 20 | 6 | 2 | 3 | 2 |
| Finger pressure | 210 | 343 | 162 | 26 | 63 | 4 |

2) 3M Clear Scotch® Tape 811 (0.75 inches), average of 3 specimens (in grams):

TABLE 2

| Roller | adhesive-to-adhesive | | | adhesive-to-steel | | |
|---|---|---|---|---|---|---|
| | Average | High | Low | Average | High | Low |
| 200 gm roller | 153 | 164 | 114 | 65 | 81 | 61 |
| Finger pressure | 295 | 343 | 285 | 103 | 114 | 181 |

As shown in the above tables, the sample adhesive film lacks substantial adhesion with light touch, but develops adhesive holding power when a proper amount of pressure is applied to activate the adhesive. Such activatable adhesion or tack-on-pressure property exists in both adhesive-to-adhesive and adhesive-to-nonadhesive contacts. In general, when the film is adhered to itself (adhesive-side to adhesive-side), the peel force is higher than when the film is adhered to other surfaces (such as glass, metal, etc.). The inventive film has many viable applications. For example, the film can be used as a non-tangling food wrap using a finger pressure as activation pressure.

Example 2

As an example of a film structure having high adhesive-to-adhesive adhesion performance and low adhesive-to-nonadhesive adhesion performance, an alternate example of the particle-coated film structure was made in accordance with the first embodiment disclosed above. Except as indicated otherwise in the following, the materials used to prepare the alternate example were identical to those in the previous example disclosed above in the first embodiment.

The thickness of the base sheet was 1500 microns ($\mu$m), and that of the adhesive was 625 microns ($\mu$m). The crosslinked polystyrene particles had an average diameter of 80 microns ($\mu$m). The particle-coated coupon was stretched with a stretch ratio of 1:3.8 in both directions in the KARO stretcher under conditions identical to the previous example. The resultant film was tested under conditions identical to the previous example except that a 4.5 lb roller instead of a 200 $\mu$m roller was used in the alternate example. As a comparison, a sample of 3M Scotch® Box Sealing Tape 355 was also tested under the same conditions. The test results are as follows.

Test protocol:

Adhesive-to-adhesive: two 1"-wide samples were laminated together with a 4.51 lb roller, and then peeled apart at 90° (T-peel) with an Instron force tester (commercially available from Instron Corporation based in Canton, Massachusetts) at 12"/minute.

Adhesive-to-steel: 1"-wide samples were laminated on a stainless steel plate with a 4.51 lb roller, and then peeled apart at 90° with an Instrumentors Inc. tester at 12"/minute.

Peel Force Test Results

Particle-coated film compared with 3M Scotch® Box Sealing Tape 355 (in grams):

TABLE 3

| Sample film type | adhesive-to-adhesive | | | adhesive-to-steel | | |
|---|---|---|---|---|---|---|
| | Average | High | Low | Average | High | Low |
| Particle coated film (1:3.8 stretch ratio) | 2767 | 2948 | 2495 | 5 | 21 | 4 |
| 3M Scotch ® Box Sealing Tape 355 | 1361 | 1451 | 1270 | 1650 | 1776 | 1590 |

As shown in Table 3, the alternate particle coated film in accordance with the present invention demonstrated a remarkable difference between its adhesive-to-adhesive peel adhesion and adhesive-to-nonadhesive (steel) peel adhesion. Surprisingly, the particle coated film demonstrated an adhesive-to-adhesive peel adhesion even higher than that of 3M Scotch® Box Sealing Tape 355.

A film with negligible adhesion to flat surfaces, but with significant adhesion to itself (adhesive-to-adhesive) can be obtained using the method described herein. Such a film may be considered to be an inexpensive adhesive analog to a mechanical fastener. Such a film may also be used to make a tape for wrapping and protecting smooth surfaces with the advantage of strong binding force obtained by turning the tape-roll around during the final wrap so as to produce adhesive-to-adhesive contact.

EXAMPLE OF THE SECOND EMBODIMENT

As an example of the second embodiment described above, a prototype film structure was made by a process comprising the following steps: (1) Co-extruding a film web; (2) Cutting; and (3) Stretching. Details of the above process are described below.

1. Co-extrusion:

A three-layer film including a top polyethylene (PE) masking layer, an adhesive layer, and a polyethylene (PE) base layer was coextruded using a three-layer feedblock attached to a 7 inch (18 cm) slot die. The thickness of the top masking layer, the adhesive layer and the base layer was 1.5 mil (0.038 mm), 10 mils (0.254 mm), and 25 mils (0.635 mm), respectively, prior to stretching.

The top and base PE resin was Mxten CM 27057-F LLDPE from Eastman Chemicals Co., Kingsport, Tenn. The adhesive blend was a 75%- 25% blend (by weight) of Kraton D 1107 from Kraton Polymers, Houston, Tex. and HL-2697 PT from H. B. Fuller Company. These are commercial materials used in hot-melt pressure sensitive adhesive (PSA) formulations. Kraton D 1107 is a styrene-isoprene-styrene block copolymer. HL-2697 PT is based on a tackified block-copolymer composition.

The top PE layer was extruded using a 0.75 inch (19.05 mm) Killion extruder with screw speed at 33 RPM and gate temperature at 470° F. (243.3° C.). The adhesive layer was extruded using a 1.25 inch (31.75 mm) Brabender extruder (C. W. Brabender, Hackensack, N.J.) with screw speed at 34 RPM and gate temperature at 400° F. (204.0° C.). The base PE was extruded using a 1.75 inch (44.45 mm) HPM extruder with screw speed at 35 RPM and gate temperature at 470° F. (243.3° C.). The feedblock and die were operated at 470° F. (243.3° C.).

The casting wheel temperature was controlled at 125° F. (51.7° C.) with the base PE contacting the wheel. The film web was pinned with air, and the surface speed of the wheel was 1.7 m/min.

2. Cutting:

The web was cut in a direction generally perpendicular to the surface of the web. The web was on a supported surface such that it was cut through a constant thickness of the web. The depth of cut was controlled by moving the support relative to the position of the cutter. A set of parallel cuts at 22.5° angle to the machine direction of the web were made. The produced cuts were parallel to each other and approximately 10 mils (0.254 mm) apart.

The web was then turned 45° and again fed through the cutter in order to create another set of parallel cuts at a 45° angle relative to the original cut direction.

In both cutting directions, the depth of cut was adjusted so that the cut was completely through the top PE layer, and approximately 50% of the way through the thickness of the adhesive layer. This was monitored using a microscope.

The resulting pattern consisted of physically isolated diamonds of the top PE layer adhered to a continuous layer of adhesive.

3. Stretching:

3 inch×3 inch (7.6 cm×7.6 cm) samples were cut out of the above cut-web and stretched in a batch stretcher. Each sample was stretched 5.5 times to a stretch ratio of 1:5.5 simultaneously in both directions at a rate of 0.25 inch (6.35 mm) per second at 115° C. The resulting film had a surface feature defined by separated diamond-shaped islands. These islands space the adhesive layer from the first major surface of the film. An approximate thickness profile of the resulting film is given as follows.

TABLE 4

| | At diamonds | | | Between diamonds | |
|---|---|---|---|---|---|
| | top layer | adhesive layer | base layer | adhesive layer | base layer |
| Thickness (in mils, 1 mil = 0.0254 mm) | 1.0 | 1.2 | 1.2 | 0.3 | 1.1 |

The base polyethylene layer was stretched relatively uniformly, while the stretched adhesive layer showed some topographical variation depending on its proximity to the diamond-shaped islands (segments 38 in FIG. 4A). This feature results in the tack-on-pressure characteristic.

Samples were tested under conditions identical to that for the peel force test of the samples in the first embodiment (Table 1).

Cut film (1 inch, 25.4 mm), average of two specimens (in grams):

TABLE 5

| Roller | adhesive-to-adhesive | | | adhesive-to-steel | | |
| --- | --- | --- | --- | --- | --- | --- |
| | Average | High | Low | Average | High | Low |
| 200 gm roller | 26 | 52 | 9 | 23 | 34 | 13 |
| Finger pressure | 114 | 150 | 66 | 62 | 73 | 54 |

As shown in Table 5, the sample film demonstrated a tack-on-pressure property similar to that of the first embodiment.

EXAMPLES OF THE THIRD EMBODIMENT

As an example of the third embodiment described above, a prototype film structure was made by a process comprising the following steps: (1) Co-extruding a film web; and (2) Stretching. Details of the above process are described below.

1. Co-extrusion:

A stemmed web with stems extending from a base layer and above an adhesive layer was cast by coextruding the adhesive and the base layer simultaneously using a microstructured tool with 900 holes per square inch (140 holes/cm$^2$), wherein each hole corresponds to a stem 48 in a molding process. The base layer was a polyethlyene-rubber copolymer SRD7587 made by Union Carbide, a subsidiary of the Dow Chemical Company, Midland Mich. The adhesive layer was made from HL-2697 PT (a tackified block copolymer) made by H. B. Fuller Company, St. Paul, Minn.

2. Stretching

Stretching was performed biaxially in the batch stretcher with a stretch ratio of 1:3.5 in each direction at 298° F. (148° C.). The strain rate was 12.5% per second based on a 2.75 inch (70 mm) gauge-length. After stretching, the height of the stems was reduced from an original height ($H_0$) of approximately 12 mil (0.3 mm) to a final height ($H_f$) of about 4.2 mil (0.11 mm). At the same time, the opening between the stems was widened from 20 mil (0.5 mm) to about 100 mil (2.5 mm) (as measured between adjacent stems). The approximate geometries of the stemmed-web and the stretched web prior to stretching are summarized as follows.

TABLE 6

| | Stem height | Top-to-top Spacing | Base thickness | Adhesive thickness |
| --- | --- | --- | --- | --- |
| Stemmed-web (in mils, 1 mil = 0.0254 mm) | 12 | 20 | 8 | 4 |
| Stretched web (in mils) | 4.2 | 100 | 0.8 | 0.2 |

The experiment illustrates that with an optimum combination of material properties and process conditions, a wide variety of finished geometries can be achieved, resulting in various film performance characteristics.

The tests and test results described above are intended solely to be illustrative, rather than predictive, and variations in the testing procedure can be expected to yield different results.

The present invention has now been described with reference to several embodiments thereof. The foregoing detailed description and examples have been given for clarity of understanding only. No unnecessary limitations are to be understood therefrom. All patents and patent applications cited herein are hereby incorporated by reference. It will be apparent to those skilled in the art that many changes can be made in the embodiments described without departing from the scope of the invention. Thus, the scope of the present invention should not be limited to the exact details and structures described herein, but rather by the structures described by the language of the claims, and the equivalents of those structures.

What is claimed is:

1. A method of forming and applying a film structure having controllable surface contact properties comprising:
   providing a multilayer film structure which has first and second major surfaces and which includes an operating agent therein, the operating agent being spaced from the first major surface of the fun structure by a top portion of the film structure, the top portion being defined by predetermined separable surface elements, and the first major surface of the film structure being defined by a plane across separable surface elements; wherein the film structure includes a top film layer, wherein the top film layer includes the separable surface elements formed by at least partially cutting the top film layer
   inelastically stretching the multilayer film structure to separate the separable surface elements across the first major surface of the film structure and to increase the exposure of the operating agent through spacings between adjacent separated separable surface elements;
   applying the first major surface of the film structure to a surface of a substrate; and
   applying pressure to the second major surface of the film such that the operating agent contacts the structure surface of the substrate.

2. The method of claim 1, wherein the top portion of the multilayer film structure comprises a layer of particles. each particle defining one of the separable surface elements.

3. The method of claim 1, wherein the film assembly includes a plurality of stems extending from a continuous portion of the film structure, each stem comprising one of the separable surface elements.

4. A method of forming a film structure comprising:
   extruding a planar film structure which has a first major surface, a second major surface, and a top portion formed by extrusion under the first major surface;
   cutting the extruded top portion of the film structure such that the top portion defines a plurality of separable surface elements where the second major surface is uncut; and
   stretching the film structure in the plain of the film at a stretch ratio of at least 1:1.05 to separate the separable surface elements across the first major surface of the film structure and to increase the exposure of an intermediate surface of the film structure through spacings between adjacent separated separable surface elements wherein when the stretch force is removed, the separated surface elements do not rejoin to their original position before stretching of the film structure and where the separated surface elements are on a continuous film structure formed by the film structure having the uncut second major surface.

5. The method of claim 4, wherein the exposed portions of the intermediate surface form a plurality of recesses, each recess having a recess face spaced from the first major surface and exposed through one of the spacings between adjacent and separated surface elements which separated surface elements are formed as islands by multiple sets of cuts at angles to each other.

6. The method of claim 4, wherein the film structure further includes an operating agent which at least partially defines the intermediate surface of the film structure.

7. The method of claim 6, wherein the operating agent is in a layer form adjacent to and beneath the top layer and wherein when the first major surface of the stretched film structure is applied to a surface of a substrate, the operating agent exhibits noticeably greater contact with the surface of the substrate when pressure is applied on the second major surface of the stretched film structure toward the surface of the substrate.

8. The method of claim 7, wherein the cutting step includes:
    completely cutting through the top film layer and partially cutting through the operating agent layer.

9. The method of claim 6, wherein the operating agent comprises an adhesive.

10. The method of claim 9, the providing step includes: coextruding the adhesive and a masking material, wherein the masking material is the top portion of the film structure.

11. The method of claim 7, wherein the pressure is a finger or hand pressure.

12. The method of claim 4, wherein the cutting step includes: completely cutting through the top layer.

13. The method of claim 4, wherein the cuffing step includes: cutting in more than one direction.

14. The method of claim 4, wherein the separable surface elements have at least a density of 100 elements per square inch before stretching.

15. The method of claim 14, wherein the separable surface elements have at least a density of 2500 elements per square inch before stretching.

16. The method of claim 15, wherein the separable surface elements have at least a density of 10,000 elements per square inch before stretching.

17. The method of claim 4, wherein the film structure is multilayered.

18. The method of claim 17, wherein the multilayer film structure is formed by coextrusion.

19. The method of claim 4, wherein the stretching step includes biaxially stretching the film structure.

20. The method of claim 4, wherein the stretching step includes simultaneously biaxially stretching the film structure.

21. The method of claim 4, wherein the stretching is inelastic stretching.

* * * * *

UNITED STATES PATENT AND TRADEMARK OFFICE
CERTIFICATE OF CORRECTION

PATENT NO.        : 7,001,475 B2                                 Page 1 of 1
APPLICATION NO.   : 10/016544
DATED             : February 21, 2006
INVENTOR(S)       : Ausen, Ronald W.

It is certified that error appears in the above-identified patent and that said Letters Patent is hereby corrected as shown below:

Column 1
Line 10, before "co-assigned" insert -- 3M Attorney Docket No. 56946US002), --.

Column 9
Line 54, delete "antiperspirants" and insert --anti-perspirants--, thereof.

Column 19
Line 51, delete "10016541" and insert --10/016,541; 3M Attorney Docket No. 56946US002), --, thereof.

Column 22
Line 24 (approx.), delete "181" and insert --81--, thereof.
Line 64, delete "4.51 lb" and insert --4.5 lb--, thereof.

Column 23
Line 2, delete "4.51" and insert --4.5 lb --, thereof.

Column 26
Line 18 (approx.), in claim 1, delete "fun" and insert --film--, thereof.
Line 38 (approx.), in claim 2, delete "particles." and insert -- particles --, thereof.

Column 28
Line 1, in claim 13, delete "cuffing" and insert --cutting--, thereof.

Signed and Sealed this

First Day of August, 2006

JON W. DUDAS
*Director of the United States Patent and Trademark Office*